US006174896B1

(12) United States Patent
Takeuchi et al.

(10) Patent No.: US 6,174,896 B1
(45) Date of Patent: Jan. 16, 2001

(54) QUINUCLIDINE DERIVATIVES AND MEDICINAL COMPOSITION THEREOF

(75) Inventors: Makoto Takeuchi; Ryo Naito; Masahiko Hayakawa; Yoshinori Okamoto; Yasuhiro Yonetoku, all of Ibaraki; Ken Ikeda, Chiba; Yasuo Isomura, Ibaraki, all of (JP)

(73) Assignee: Yamanouchi Pharmaceutical Co., Ltd., Tokyo (JP)

( * ) Notice: Under 35 U.S.C. 154(b), the term of this patent shall be extended for 0 days.

(21) Appl. No.: 09/312,392

(22) Filed: May 14, 1999

Related U.S. Application Data

(63) Continuation of application No. 08/860,377, filed as application No. PCT/JP95/02713 on Dec. 27, 1995, now Pat. No. 6,017,927.

(30) Foreign Application Priority Data

Dec. 28, 1994 (JP) .................................................. 6-327045

(51) Int. Cl.[7] ...................... A61K 31/439; C07D 453/02
(52) U.S. Cl. ............................................ 514/305; 546/137
(58) Field of Search ............................ 546/137; 514/305

(56) References Cited

FOREIGN PATENT DOCUMENTS

| | | |
|---|---|---|
| 2 0309424 | 3/1989 | (EP) . |
| 1 424021 | 4/1991 | (EP) . |
| 1 0247266 | 12/1997 | (EP) . |
| 2 249093 | 4/1992 | (GB) . |
| 95 06635 | 3/1995 | (JP) . |
| 7-258250 | 10/1995 | (JP) . |
| WO 92/06958 | 4/1992 | (WO) . |
| WO 93/16048 | 8/1993 | (WO) . |

*Primary Examiner*—Patricia L. Morris
(74) *Attorney, Agent, or Firm*—Sughrue, Mion, Zinn, Macpeak & Seas, PLLC

(57) ABSTRACT

Quinuclidine derivatives represented by general following general formula (I), salts, N-oxides or quaternary ammonium salts thereof, and medicinal compositions containing the same.

(I)

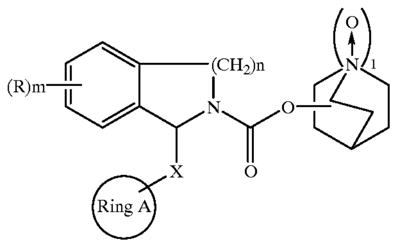

The compound has an antagonistic effect on muscarinic $M_3$ receptors and is useful as a preventive or remedy for urologic diseases, respiratory diseases or digestive diseases.

6 Claims, No Drawings

QUINUCLIDINE DERIVATIVES AND MEDICINAL COMPOSITION THEREOF

This is a continuation of application Ser. No. 08/860,377 filed Jun. 25, 1997 now U.S. Pat. No. 6,017,927, the disclosure of which is incorporated herein by reference which is a 371 of PCT JP 95/02713, filed Dec. 27, 1995.

TECHNICAL FIELD

This invention relates to medicines, particularly quinuclidine derivatives or their salts, N-oxides or quaternary ammonium salts having muscarinic receptor antagonistic activities and also to pharmaceutical compositions containing such compounds.

BACKGROUND ART

Studies have been made on the muscarinic receptor, and it is known that compounds having muscarinic receptor antagonistic activities cause bronchodilation, suppression of gastrointestinal motility, suppression of acid secretion, dry mouth, mydriasis, suppression of bladder contraction, hypohidrosis, tachycardia, or the like. It is known that the muscarinic receptor includes at least three subtypes. The $M_1$ receptor mainly exists in the brain or the like, the $M_2$ receptor in the heart or the like, and the $M_3$ receptor in the smooth muscles or gland tissues.

A number of such compounds having muscarinic receptor antagonistic activities are hitherto known and, for example, atropine is a typical example ("The MERCK INDEX, ELEVENTH EDITION", p. 138). However, atropine antagonizes the $M_1$, $M_2$ and $M_3$ receptors non-selectively, so that it is difficult to use it for the treatment of a specific disease. In recent years, according to the progress of the studies on the subtypes of the muscarinic receptor, compounds having selective antagonistic activities against the $M_1$, $M_2$ or $M_3$ receptor have been investigated (an unexamined published British Patent Application No. 2,249,093, an unexamined published Japanese Patent Application (kokai) 1-131145, and an unexamined published Japanese Patent Application (kokai) 3-133980). There is a demand for a compound having selective antagonistic activity against muscarinic $M_3$ receptor among these three subtypes and is free from the cardiac side effects resulting from the $M_2$ receptor.

The compound represented by the following general formula is described in an unexamined published Japanese Patent Application (kokai) 62-252764.

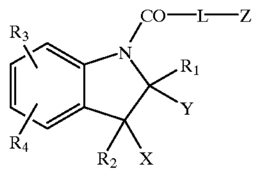

(wherein L represents NH or O;

X and Y each independently represents a hydrogen atom or a $C_{1-6}$ alkyl-group or they may be combined together to form a bond;

$R_1$ and $R_2$ each independently represents a hydrogen atom, a $C_{1-6}$ alkyl group . . . (omission) . . . ;

$R_3$ and $R_4$ each independently represents a hydrogen atom, a halogen atom, $CF_3$, a $C_{1-6}$ alkyl group . . . (omission) . . . , a phenyl group, an amino group which may optionally be N-substituted by one or two groups selected from phenyl, $C_{1-6}$ alkyl groups or may optionally be N-disubstituted by $C_{6-8}$ polyethylene . . . (omission) . . . ;

Z represents

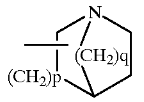

or the like;

p is 1 or 2; and q is 1–3.

The compound described in the above patent literature is disclosed as a 5-HT antagonist and no disclosure about the muscarinic receptor antagonistic activity is found. The above compound is clearly distinguished from the compound according to the present invention in pharmacological effects.

DISCLOSURE OF THE INVENTION

The inventors of the present application have carried out extensive studies on compounds having the above-described muscarinic $M_3$ receptor antagonistic activities. As a result, we created novel quinuclidine derivatives having a basic skeleton different from that of the conventional compound, and found that such compounds have excellent selective antagonistic activity against muscarinic $M_3$ receptor, resulting in the completion of the present invention.

Thus, the compounds of the present invention relate to quinuclidine derivatives represented by the following general formula (I); their salts, N-oxides or quaternary ammonium salts; pharmaceutical compositions comprising said compounds or salts thereof and pharmaceutically acceptable carriers, particularly to muscarinic $M_3$ receptor antagonists.

(I)

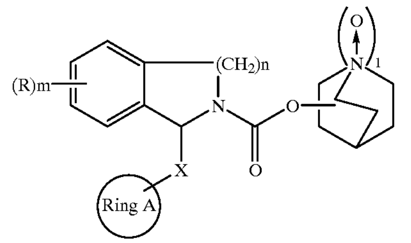

(symbols in the formula have the following meanings:

Ring A: an aryl group, a cycloalkyl group, a cycloalkenyl group, a heteroaryl group having 1 to 4 hetero atoms selected from the group consisting of an oxygen atom, a nitrogen atom and a sulfur atom or a 5- to 7-membered saturated heterocyclic group, wherein said ring may be substituted by an optional substituent;

X: a single bond or a methylene group;

R: a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group or a lower alkyl group which may be substituted by a halogen atom, a hydroxyl group, a lower alkoxy group, an amino group or a mono- or di-lower alkylamino group;

l: 0 or 1, m: 0 or an integer of 1 to 3, and n: an integer of 1 or 2, hereinafter the same apply similarly)

Among the compound (I) of the present invention, particularly preferred compounds are quinuclidine derivatives wherein the ring A represents an aryl group, a cycloalkyl group, a cycloalkenyl group, a heteroaryl group having 1 to 4 hetero atoms selected from the-group consisting of an oxygen atom, a nitrogen atom and a sulfur atom or a 5- to 7-membered saturated heterocyclic group, in which such a ring may be substituted by a substituent selected from the group consisting of a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group, and a lower alkyl group which may be substituted by a halogen atom, a hydroxyl group, a lower alkoxy group, an amino group or a mono- or di-lower alkylamino group, and their salts, N-oxides or quaternary ammonium salts;

quinuclidine derivatives wherein R represents a halogen atom, a lower alkyl group, a hydroxyl group, a lower alkoxy group, a nitro group, a cyano group, an amino group or a mono- or di-lower alkylamino group, and the ring A represents an aryl group, a cycloalkyl group, a cycloalkenyl group, a 5- or 6-membered monocyclic heteroaryl group having 1 to 4 hetero atoms selected from the group consisting of an oxygen atom, a nitrogen atom and a sulfur atom or a 5- to 7-membered saturated heterocyclic group, in which such a ring may be substituted by a halogen- atom, a lower alkyl group, a hydroxyl group, a lower alkoxy group, a nitro group, a cyano group, an amino group or a mono- or di-lower alkylamino group, and their salts, N-oxides or quaternary ammonium salts;

quinuclidine derivatives wherein m is 0, and the ring A represents an aryl group, a cycloalkyl group or a cycloalkenyl group which may be substituted by a halogen atom, a lower alkyl group, a hydroxyl group or a lower alkoxy group, or a 5- or 6-membered monocyclic heteroaryl group having 1 to 4 hetero atoms selected from the group consisting of an oxygen atom, a nitrogen atom and a sulfur atom, and their salts, N-oxides or quaternary ammonium salts;

quinuclidine derivatives wherein the ring A represents a phenyl group which may be substituted by a halogen atom or a lower alkyl group, a cycloalkyl group, a pyridyl group, a furyl group or a thienyl group, and their salts, N-oxides or quaternary ammonium salts;

quinuclidine derivatives wherein X represents a single bond, and their salts, N-oxides or quaternary ammonium salts; and quinuclidine derivatives wherein n is 2, and their salts, N-oxides or quaternary ammonium salts.

The present invention also provides muscarinic $M_3$ receptor antagonists which comprise quinuclidine derivatives (I) or their salts, N-oxides or quaternary ammonium salts, that is, the compound (I) of the present invention and pharmaceutically acceptable carriers, preferably agents for the prevention and/or treatment of urinary diseases (e.g., neurogenic pollakiuria, neurogenic bladder, nocturnal enuresis, unstable bladder, cystospasm and chronic cystitis), or respiratory diseases (e.g., chronic obstructive pulmonary diseases, chronic bronchitis, asthma and rhinitis).

Hereinafter, the compound (I) of the present invention will be described in detail.

Different from the conventional muscarinic $M_3$ receptor antagonist, the compound (I) of the present invention is structurally characterized in that it has as a basic skeleton a tetrahydroisoquinoline skeleton (Ia) or isoindoline skeleton (Ib) having a quinuclidinyloxycarbonyl group, etc. bonded to the nitrogen atom in the ring as shown below.

(Ia)

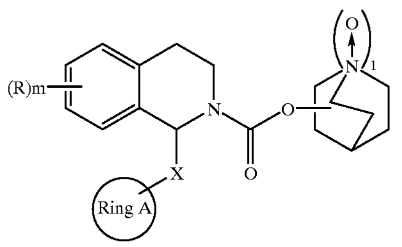

(Ib)

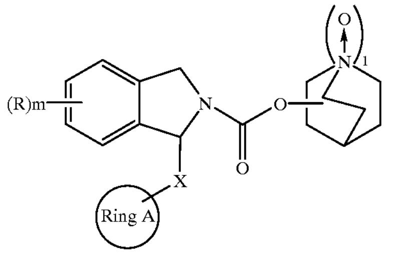

Furthermore, the compound (I) of the present invention is characterized in that it has ring A, that is, a cyclic group selected from an aryl group, a cycloalkyl group, a cycloalkenyl group, a heteroaryl group having 1 to 4 hetero atoms selected from the group consisting of an oxygen atom, a nitrogen atom and a sulfur atom or a 5- to 7-membered saturated heterocyclic group, at the 1-position of the tetrahydroisoquinoline or isoindoline through X.

Unless otherwise specified, the term "lower" as used in the definition of the general formula in this specification means a linear or branched carbon chain having 1 to 6 carbon atoms. Accordingly, the "lower alkyl group" means linear or branched alkyl group having 1 to 6 carbon atoms. Specific examples include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Among these groups, alkyl groups having 1 to 4 carbon atoms such as methyl, ethyl, propyl, isopropyl and butyl groups are preferred,- and a methyl group is more preferred.

The "aryl group" means aromatic hydrocarbon groups and preferably aryl groups having 6 to 14 carbon atoms. Specific examples include phenyl, naphthyl, indenyl, anthryl and phenanthryl groups, and a phenyl group is more preferred.

Examples of the "cycloalkyl group" include those having 3 to 8 carbon atoms, such as cyclopropyl, cyclobutyl, cyclopentyl, cyclohexyl, cycloheptyl and cyclooctyl. Among these groups, cyclopropyl, cyclobutyl, cyclopentyl and cyclohexyl groups are preferred, and a cyclohexyl group is more preferred.

Examples of the "cycloalkenyl group" include those having 3 to 8 carbon atoms such as 1-cyclopropenyl, 2-cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl, 1-cyloheptenyl, 2-cycloheptenyl, 3-cycloheptenyl, 4-cycloheptenyl, 1-cyclooctenyl, 2-cyclooctenyl, 3-cyclooctenyl, 4-cyclooctenyl, 2,4-cyclopentadienyl, 2,5-cyclohexadienyl, 2,4-cycloheptadienyl, and 2,6-cycloheptadienyl.

The "heteroaryl group containing 1 to 4 hetero atoms selected from the group consisting of an oxygen atom, a nitrogen atom and a sulfur atom" means a 5- or 6-membered heteroaryl group which may be condensed with a benzene ring. Specific examples include 5- or- 6-membered monocyclic heteroaryl groups containing 1 to 4 hetero atoms selected from the group consisting of an oxygen atom, a nitrogen atom and a sulfur atom, such as furyl, thienyl, pyrrolyl, imidazolyl, pyrazolyl, triazolyl, tetrazolyl, isothiazolyl, isoxazolyl, pyridyl, pyrazinyl, pyrimidinyl and pyridazinyl groups; and 5- or 6-membered heteroaryl groups condensed with a benzene ring, such as indolyl, indazolyl, indolizinyl, quinolyl, quinazolinyl, quinolizinyl, quinoxalinyl, cinnolinyl, benzimidazolyl, benzofuranyl, dihydrobenzofuranyl, benzoisoxazolyl, benzooxazolyl, benzothiazolyl and benzothienyl groups.

Among these groups, preferred are 5- or 6-membered monocyclic heteroaryl groups containing 1 to 4 hetero atoms selected from the group consisting of an oxygen atom, a nitrogen atom and a sulfur atom, and furyl, thienyl and pyridyl groups are more preferred.

The "5- to 7-membered saturated heterocyclic group" means a 5-, 6- or 7-membered saturated heterocyclic group containing 1 to 2 oxygen, nitrogen and/or sulfur atoms. Specific examples include pyrrolidinyl, imidazolydinyl, piperidinyl, piperazinyl and morpholinyl groups.

The "aryl group", "cycloalkyl group", "cycloalkenyl group", "heteroaryl group containing 1 to 4 hetero atoms selected from the group consisting of an oxygen atom, a nitrogen atom and a sulfur atom", "5- or 6-membered monocyclic heteroaryl group containing 1 to 4 hetero atoms selected from the group consisting of an oxygen atom, a nitrogen atom and a sulfur atom", or "5- to 7-membered saturated heterocyclic group" as the group A may be substituted by an optional substituent. The number of the substituent is not limited to one but may be plural. Any group that can substitute for such a ring can be employed as the optional substituent. Preferred examples include a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group and a lower alkyl group which may be substituted by a halogen atom, a hydroxyl group, a lower alkoxyl group, an amino group or a mono- or di-lower alkylamino group; a halogen atom, a lower alkyl group, a hydroxyl group, a lower alkoxy group, a nitro group, a cyano group, an amino group and a mono- or di-lower alkylamino group are more preferred; a halogen atom, a lower alkyl group, a hydroxyl group and a lower alkoxy group are still more preferred; and a halogen atom and a lower alkyl group are particularly preferred.

Examples of the halogen-atom include fluorine, chlorine, bromine and iodine. When the substituent is a halogen atom, the number of the substituents is not particularly limited. When two or more halogen atoms are substituted, any combination of the above atoms is possible. Examples of the halogen atom-substituted lower alkyl group include fluoromethyl, chloromethyl, bromomethyl, iodomethyl, 1-fluoroethyl, 1-chloroethyl, 1-bromoethyl, 2-chloroethyl, 2-bromoethyl, dichloromethyl, trifluoromethyl, trichloromethyl, tribromomethyl, triiodomethyl and dichlorobromomethyl. Among these groups, a trifluoromethyl group is preferred.

Examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy and hexyloxy. Among these groups, lower alkoxy groups containing an alkyl group having 1 to 4 carbon atoms, such as methoxy, ethoxy, propoxy and butoxy are preferred, and methoxy and ethoxy groups are more preferred.

Examples of the lower alkoxycarbonyl group include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxy (amyloxy)carbonyl, isopentyloxycarbonyl, tert-pentyloxycarbonyl, neopentyloxycarbonyl, 2-methylbutoxycarbonyl, 1,2-dimethylpropoxycarbonyl, 1-ethylpropoxycarbonyl and hexyloxycarbonyl.

Examples of the "lower acyl group" include formyl, acetyl, propionyl, butyryl, valeryl and pivaloyl, and formyl, acetyl and propionyl are preferred.

The "lower alkylthio group" means a mercapto group of which hydrogen atom has been substituted by the above-exemplified lower alkyl group, such as methylthio, ethylthio, propylthio, isopropylthio, butylthio, pentylthio and hexylthio groups.

Examples of the "lower alkylsulfonyl group" include methylsulfonyl, ethylsulfonyl, propylsulfonyl, isopropylsulfonyl, butylsulfonyl, pentylsulfonyl and hexylsulfonyl.

Examples of the "lower alkylsulfinyl group" include methylsulfinyl, ethylsulfinyl, propylsulfinyl, isopropylsulfinyl, butylsulfinyl, pentylsulfinyl and hexylsulfinyl.

Examples of the "lower alkanesulfonamido group" include methanesulfonamido, ethanesulfonamido, propanesulfonamido, isopropanesulfonamido, butanesulfonamido, pentanesulfonamido and hexanesulfonamido.

The "mono- or di-lower alkylcarbamoyl group" means a carbamoyl group in which one or two hydrogen atom(s) have been substituted by the above-exemplified lower alkyl group(s), such as methylcarbamoyl, ethylcarbamoyl, propylcarbamoyl and dimethylcarbamoyl groups.

The "mono- or di-lower alkylamino group" means an amino group in which one or two hydrogen atom(s) have been substituted by the above-exemplified lower alkyl group (s), such as methylamino, ethylamino, propylamino, dimethylamino, diethylamino and dipropylamino groups.

The term "lower alkyl group which may be substituted by a halogen atom, a hydroxyl group, a lower alkoxy group, an amino group or a mono- or di-lower alkylamino group"

means a lower alkyl group in which at least one optional hydrogen atom has been substituted by a halogen atom, a hydroxyl group, a lower alkoxy group, an amino group or a mono- or di-lower alkylamino group. The lower alkyl group substituted by a halogen atom is as described in the above description of the halogen atom.

The compound (I) of the present invention contains a quinuclidinyl group. The nitrogen atom of the quinuclidinyl group may form oxide (l=1) or quaternary ammonium salt. Where a quaternary ammonium salt is formed, specific examples of the group bound to the nitrogen atom include lower alkyl, lower alkenyl-and lower alkynyl.

The term "lower alkenyl" as used herein means a linear or branched alkenyl group having 2 to 6 carbon atoms, such as vinyl, propenyl, butenyl, methylpropenyl, dimethylvinyl, pentenyl, methylbutenyl, dimethylpropenyl, ethylpropenyl, hexenyl, dimethylbutenyl and methylpentenyl. Among these groups, a propenyl group is preferred.

The "lower alkynyl group" means a linear or branched alkynyl group having 2 to 6 carbon atoms, such as ethynyl, propynyl, butynyl, methylpropynyl, pentynyl, methylbutynyl and hexynyl groups. Among these groups, alkynyl groups having 2 to 3-carbon atoms such as ethynyl and propynyl are preferred.

The anion for the quaternary ammonium salt is not particularly limited and the examples include ions of a halogen atom, triflate, tosylate and mesylate, preferably ions of a halogen atom, i.e. halide ions (e.g., chloride ion, bromide ion, iodide ion and triiodide ion). Examples of other anions include inorganic anions such as nitrate ion, sulfate ion, phosphate ion and carbonate ion, carboxylates such as formate ($HCOO^-$), acetate ($CH_3COO^-$), propionate, oxalate and malonate, and amino acid anions such as glutamate. Among the halide ions, bromide ion and iodide ion are preferred. Incidentally, the anion can be converted into a preferable anion as needed by the ordinary ion exchange reaction.

The compound (I) of the present invention contains an asymmetric carbon atom so that there exist optical isomers based on it. In addition, some of the invention compounds have stereoisomers or tautomers. The present invention also embraces diastereomers and enantiomers obtained by the separation of the above isomers as well as mixtures thereof.

Some of the compounds (I) of the present invention can form salts with an acid as well as the above-described quaternary ammonium salts with a quinuclidynyl group. Examples of such salt include acid addition salts with a mineral acid such as hydrochloric acid, hydrobromic acid, hydroiodic acid, sulfuric acid, nitric acid or phosphoric acid; and those with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid or glutamic acid. The compounds (I) of the present invention also embrace hydrates, solvates with ethanol or the like, and substances in any polymorphism crystals.

Preparation Process

The compound (I) of the present invention can be prepared in accordance with various processes. The typical preparation processes are explained below.

First Preparation Method

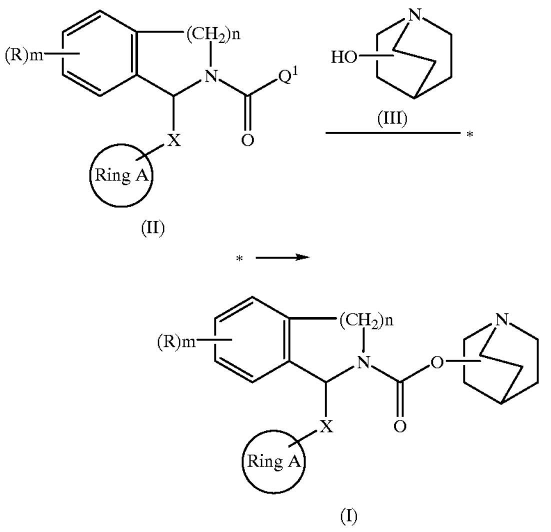

(in the formula, $Q^1$ represents a leaving group which is advantageous in the present reaction, and ring A, R, X, m and n have the same meanings as defined above. Hereinafter, the same will apply similarly).

This reaction is carried out by stirring the compound represented by the general formula (II) and quinuclidinol represented by the general formula (III) in an amount corresponding to the reaction in an inert solvent at room temperature or under heating.

The leaving group $Q^1$ embraces, for example, a halogen atom, a lower alkoxy group, a phenoxy group and an imidazolyl group.

Examples of the inert solvent include dimethylformamide (DMF), dimethylacetamide, tetrahydrofuran (THF), dioxane, dimethoxyethane, diethoxyethane, benzene, toluene and xylene and mixed solvents thereof.

It is preferable to add a base (e.g., sodium, sodium hydride, sodium methoxide and sodium ethoxide) in order to accelerate the present reaction.

Second Preparation Method

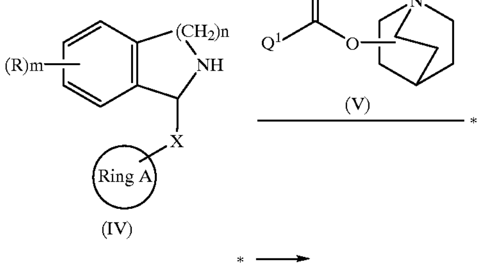

-continued

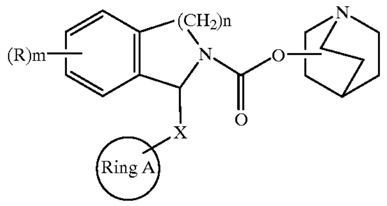

(I)

(wherein the ring A, R, X, m, n and $Q^1$ have the same meanings as defined above.)

This reaction is carried out by stirring the compound represented by the general formula (IV) and the compound represented by the general formula (V) in the above-described inert solvent at room temperature or under heating.

It is preferable to add a base (e.g., sodium, sodium hydride, sodium methoxide, sodium ethoxide, triethylamine and pyridine) in order to accelerate the present reaction.

Other Preparation Methods

Among the compounds of the present invention, a compound in which the nitrogen atom of the quinuclidinyl group forms oxide or a quaternary ammonium salt can be prepared by N-oxide formation or N-alkylation of a tertiary amine compound in the compounds of the present invention.

The N-oxide formation reaction can be carried out by the oxidation reaction in a conventional manner, more specifically, by stirring a tertiary amine compound in the compounds of the present invention and a corresponding amount or excess amount of oxidizing agent in an inert solvent such as chloroform, dichloromethane or dichloroethane, an alcohol such as methanol or ethanol or water or a mixed solvent thereof under cooling or at room temperature, or in some cases under heating. Examples of the oxidizing agent include organic peracids such as m-chloroperbenzoic acid, sodium periodate and hydrogen peroxide.

The N-alkylation reaction can be carried out in accordance with the conventional N-alkylation reaction, more specifically by stirring a tertiary amine compound in the compound of the present invention and a corresponding amount of an alkylating agent in an inert solvent such as dimethylformamide, chloroform, benzene, 2-butanone, acetone or tetrahydrofuran under cooling or a room temperature, or in some cases under heating.

Examples of the alkylating agent include lower alkyl halides, lower alkyl trifluoromethanesulfonates, lower alkyl p-toluenesulfonates and lower alkyl methanesulfonates, preferably lower alkyl halides.

For the preparation of the compound of the present invention, it is sometimes necessary to protect a functional group. In such a case, introduction of a proper protecting group and deprotection operation in a conventional manner are carried out additionally.

The compound of the present invention so prepared is provided as is in the free form, or after subjected to the salt formation treatment in a conventional manner, it is isolated and purified as its salt. Isolation and purification are carried out by the ordinary chemical operation such as extraction, concentration, evaporation, crystallization, filtration, recrystallization or a variety of chromatography.

INDUSTRIAL APPLICABILITY

The compound of the present invention has affinity and selectivity for the muscarinic $M_3$ receptor and, as an $M_3$ receptor antagonist, it is useful as an agent for prevention or treatment of various $M_3$ receptor-related diseases, particularly urinary diseases such as urinary incontinence or pollakiuria in neurogenic pollakiuria, neurogenic bladder, nocturnal enuresis, unstable bladder, cystospasm or chronic cystitis; respiratory diseases such as chronic obstructive pulmonary diseases, chronic bronchitis, asthma or rhinitis; or digestive diseases such as irritable bowel syndrome, spastic colitis or diverticulitis.

In particular, the compound of the present invention has high selectivity for the $M_3$ receptor existing in the smooth muscle or gland tissues compared with the $M_2$ receptor existing in the heart or the like, so that it has high utility as an $M_3$ receptor antagonist having less side effects on the heart or the like, particularly as an agent for prevention or treatment of urinary incontinence, pollakiuria, chronic obstructive pulmonary diseases, chronic bronchitis, asthma or rhinitis.

The affinity and antagonism of the compound of the present invention for the muscarinic receptor was confirmed by the following tests.

Muscarinic receptor affinity test (in vitro)

a. Preparation of membranes

From a male Wistar rat (Japan SLC), the heart and submandibular gland were excised, mixed with a 20 mM HEPES buffer (pH 7.5, which will hereinafter be abbreviated as "HEPES buffer") containing 5 times the volume of 100 mM sodium chloride and 10 mM magnesium chloride was added, followed by homogenization under ice-cooling. The resulting mixture was filtered through gauze, followed by ultracentrifugation at 50,000×g and 4° C. for 10 minutes. The precipitate obtained was suspended in an HEPES buffer, followed by further ultracentrifugation at 50,000×g and 4° C. for 10 minutes. The precipitate obtained was suspended in an HEPES buffer. The resulting suspension was stored at −80° C. and provided for the test after melting upon use.

b. Muscarinic $M_2$ receptor binding test

The test was carried out in accordance with the method of Doods et al. (*J. Pharmacol. Exp. Ther.*, 242, 257–262, 1987) with some modifications. The cardiac membrane sample, [$^3$H]-quinuclidinyl benzilate and the test compound were incubated in a 0.5 ml HEPES buffer at 25° C. for 45 minutes, followed by suction filtration through a glass filter (Whatman GF/B). The filter was washed three times with 5 ml portions of an HEPES buffer. The radioactivity of the [$^3$H]-quinuclidinyl benzilate adsorbed on the filter was measured by a liquid scintillation counter. Incidentally, nonspecific binding of the receptor was determined by the addition of 1 $\mu$M atropine. The affinity of the compound of the present invention for the muscarinic $M_2$ receptor was determined from a dissociation constant (Ki) calculated, in accordance with Chen and Prusoff (*Biochem. Pharmacol.* 22, 3099, 1973), based on the concentration ($IC_{50}$) of the test compound at which 50% of the binding of the [$^3$H]-quinuclidinyl-benzilate, that is, a labeled ligand was inhibited.

c. Muscarinic $M_3$ receptor binding test

In a similar manner to the above muscarinic $M_2$ receptor binding test except that the submandibular gland was used as a membrane sample and [$^3$H]-N-methylscopolamine was used as a labeled ligand, a muscarinic $M_3$ receptor binding test was carried out.

Results: The compound (I) of the present invention had a Ki value of from $10^{-8}$ to $10^{-10}$ for $M_3$ receptor, which suggested that the affinity for $M_3$ receptor was at least 10 times as high as that for $M_2$ receptor.

Muscarinic receptor antagonism test (in vivo)

a. Test on rhythmic bladder contraction in rat

A female Wistar rat (130–200 g) was subjected to urethane anesthesia (1.0 g/kg s.c.), followed by ligation of the ureter on the kidney side. A urethral catheter was allowed to remain in the bladder, and about 1.0 ml of physiological saline was injected into the bladder through the catheter to cause rhythmic bladder contraction. Intravesical pressure was measured by a pressure transducer. After rhythmic contraction continued stable for at least 5 minutes, the test compound was cumulatively administered from the external jugular vein. Five to ten minutes later, the intravesical pressure was measured. An inhibition ratio of bladder contraction was determined compared with the bladder contraction before administration of the test compound and the dose of the test compound required for 30% inhibition of the bladder contraction before administration was designated as $ED_{30}$.

As a result of the test, the compound of the present invention showed good $ED_{30}$ value.

b. Test on salivary secretion in rat

A male Wistar rat (160–190 g) was subjected to anesthesia with urethane (0.8 g/kg i.p.), and the test compound was administered (to the control group: solvent). Fifteen minutes later, 0.8 μmol/kg of oxotremorine was administered. In each case, the drug was administered through its femoral artery. The saliva secreted for 5 minutes after the administration of oxotremorine was collected and weighed. The inhibition ratio against the amount of saliva in the control group was determined and the dose of the test compound required for 50% inhibition of the amount of saliva in the control group was designated as $ID_{50}$.

As a result of the test, the $ID_{50}$ value of atropine tested as a comparative compound was substantially the same with the $ED_{30}$ value obtained in the above rat rhythmical bladder contraction test, while the $ID_{50}$ value of the invention compound was at least 5 times as much as the above-described $ED_{30}$ value, which suggested that the compound of the present invention has relatively weak action against the salivary secretion.

c. Test on bradycardia in rat

The test was carried out in accordance with the method of Doods et al. (*J. Pharmacol. Exp. Ther.,* 242, 257–262, 1987). A male Wistar rat (250–350 g) was subjected to anesthesia with pentobarbital sodium (50 mg/kg i.p.). The neck region was excised, followed by the division of right and left vagus nerves. After a cannula was inserted into a trachea to secure airway, a stainless rod was inserted from the orbit and the spinal cord was destroyed. Under artificial respiration (at 10 cc/kg and 50 times/minute), the rectal temperature was maintained at 37.5° C. and a heart rate was monitored at the common carotid artery. An indwelling needle was fixed to the femoral artery, from which the drug was administered. After the destruction of the spinal cord, the rat was allowed to stand for 15 minutes to attain the equilibrium, followed by the administration of atenolol (10 mg/kg). After the equilibration for additional 15 minutes, the test compound was administered. Fifteen minutes later, oxotremorine was cumulatively administered, thereby the reduction in the heart rate was measured. The amount of the test compound required for 10-times rightward shift of the dose-response curve of the control group was designated as $DR_{10}$.

Results: The compound (I) of the present invention had sufficiently low activity against bradycardia and no bradycardia was observed at the-administration amount of several mg/kg.

As a result of the above-described muscarinic receptor affinity test (in vitro), it was found that the compound (I) of the present invention had selectivity and high affinity for $M_3$ receptor. Even in the muscarinic receptor antagonism test (in vivo), the compound of the present invention showed good muscarinic $M_3$ antagonistic activity but low activity on the bradycardia having relationship with muscarinic $M_2$ receptor. Accordingly, it was found that the compound (I) of the present invention has selective antagonistic activity against muscarinic $M_3$ receptor, and furthermore, it has less side effects such as dry mouth compared with the conventional anti-cholinergic agent.

A pharmaceutical composition containing one or more of the compounds of the present invention and salts thereof is prepared using an ordinary pharmaceutically acceptable carrier.

In the present invention, the administration of the pharmaceutical composition can be carried out either orally or parenterally in the form of an injection, suppository, transdermal agent, inhalant or intravesical injection.

The dose is optionally determined in each case in consideration of the conditions, age, sex and the like of the patient to be administered. In the oral administration, the daily dose may generally range from about 0.01 mg/kg to 100 mg/kg per adult. It is administered once or in 2–4 portions. Where intravenous administration is adopted in consideration of the conditions of the patient, the daily dose may generally range from about 0.001 mg/kg to 10 mg/kg per adult, once or plural portions per day.

Examples of the pharmaceutical carrier include nontoxic solid or liquid pharmaceutical substances.

Examples of the solid composition for the oral administration include tablets, pills, capsules, powders and granules, or the like. In such solid compositions, one or more active substances are mixed with at least one inert diluent such as lactose, mannitol, glucose, hydroxypropylcellulose, microcrystalline cellulose, starch, polyvinylpyrrolidone, agar, pectin, magnesium metasilicate or magnesium aluminate. In the composition, it is possible to incorporate additives other than the above inert diluent, for example, a lubricant such as magnesium stearate, a disintegrator such as cellulose calcium glycolate, a stabilizer such as lactose, a solubilization aid such as glutamic acid or aspartic acid in a conventional manner. A tablet or pill may optionally be coated with sugar or a film of a gastric or enteric substance such as sucrose, gelatin, hydroxypropylcellulose or hydroxypropylmethylcellulose phthalate.

Examples of the liquid composition for oral administration include pharmaceutically acceptable emulsions, solutions, suspensions, syrups and elixirs which contain a commonly employed inert diluent such as purified water or ethanol. The composition can also contain, in addition to such an inert diluent, a wetting agent, auxiliary agent such as suspending agent, sweetener, flavoring agent, aroma and/or antiseptic.

The injection for parenteral administration according to the present invention include a sterile aqueous or nonaqueous solution, suspension or emulsion. Examples of the aqueous solution and suspension include distilled water and physiological saline for injection. Examples of the non-water-soluble solution or suspension include ethylene glycol, polypropylene glycol, polyethylene glycol, vegetable oils such as cacao butter, olive oil or sesame oil, alcohols such as ethanol, gum arabic and "Polysolvate 80" (trade name). Such a composition may further contain an isotonicity agent, antiseptic agent, wetting agent, emulsifying agent, dispersing agent, stabilizer (for example, lactose) and/or solubilizing aid (for example, glutamic acid, aspartic acid). They are sterilized by, for example, filtration through a bacteria-retaining filter, incorporation of a sterilizer, or irradiation. Alternatively, a sterile solid composition which has been prepared in advance is dissolved in sterile water or a sterile injection solvent upon use.

BEST MODES FOR CARRYING OUT THE INVENTION

The present invention will hereinafter be described in further detail with reference to the following Examples. However, the compounds of the present invention should not be construed as being limited to the compounds which will be described later in Examples but embrace all the compounds represented by the above formula (I) and salts, hydrates, solvates, geometrical and optical isomers and any polymorphism forms of the compound (I).

Incidentally, the starting compounds for the compound of the present invention include novel compounds and preparation examples of such starting compounds will be described below as Reference Examples.

REFERENCE EXAMPLE 1

To a 130 ml dichloromethane solution containing 6.28 g of 1-phenyl-1,2,3,4-tetrahydroisoquinoline and 3.34 g of triethylamine, 3.1 ml of ethyl chloroformate was added dropwise under ice-cooling, followed by stirring at room temperature overnight. The reaction solution was washed successively with water, 1N hydrochloric acid, water and brine and then dried over anhydrous sodium sulfate. The solvent was removed under reduced pressure, thereby 10.58 g of ethyl 1-phenyl-1,2,3,4-tetrahydro-2-isoquinolinecarboxylate was obtained as pale yellow oil.

Infrared absorption spectrum νmax(neat)$cm^{-1}$: 1700, 1430, 1296, 1230, 1122.

Nuclear magnetic resonance spectrum ($CDCl_3$, TMS internal standard)

δ: 1.29 (3H, t, J=7.3 Hz), 2.75–3.45 (3H, m), 3.90–4.40 (1H, m), 4.21 (2H, q, J 7.3 Hz), 6.38 (1H, s), 6.95–7.45 (9H, m).

In a similar manner to Reference Example 1, the compounds of the following Reference Examples 2 to 14 were obtained.

REFERENCE EXAMPLE 2

Methyl 1-phenyl-2-isoindolinecarboxylate Starting compounds: 1-phenylisoindoline, methyl chloroformate Infrared absorption spectrum νmax(KBr)$cm^{-1}$: 1708, 1460, 1376, 1100

Nuclear magnetic resonance spectrum ($CDCl_3$, TMS internal standard)

δ: 3.60, 3.72 (3H, s×2), 4.89, 4.96 (2H, s×2), 5.94, 6.03 (1H, s×2), 6.95–7.10 (1H, m), 7.15–7.35 (8H, m)

REFERENCE EXAMPLE 3

Ethyl 1-(4-pyridyl)-1,2,3,4-tetrahydro-2-isoquinolinecarboxylate

Starting compound: 1-(4-pyridyl)-1,2,3,4-tetrahydroisoquinoline

Properties: pale yellow oil

Mass analysis (m/z, EI): 282 ($M^+$)

Nuclear magnetic resonance spectrum ($CDCl_3$, TMS internal standard)

δ: 1.29 (3H, t, J=7.1 Hz), 2.60–3.45 (3H, m), 3.85–4.20 (1H, m), 4.22 (2H, q, J=7.1 Hz), 6.31 (1H, s), 7.14 (2H, dd, J=4.4, 1.5 Hz), 7.17–7.26 (4H, m), 8.51 (2H, dd, J=4.4, 1.5 Hz)

REFERENCE EXAMPLE 4

Ethyl 1,2,3,4-tetrahydro-1-(2-thienyl)-2-isoquinolinecarboxylate

Starting compound: 1,2,3,4-tetrahydro-1-(2-thienyl)isoquinoline

Properties: pale yellow oil

Mass analysis (m/z, EI): 287 ($M^+$)

Nuclear magnetic resonance spectrum ($CDCl_3$, TMS internal standard)

δ: 1.32 (3H, t, J=7.3 Hz), 2.65–3.60 (3H, m), 4.00–4.30 (1H, m), 4.23 (2H, q, J=7.3 Hz), 6.53 (1H, s), 6.70–6.95 (2H, m), 7.15–7.30 (5H, m)

REFERENCE EXAMPLE 5

Ethyl 1,2,3,4-tetrahydro-1-(3-thienyl)-2-isoquinolinecarboxylate

Starting compound: 1,2,3,4-tetrahydro-1-(3-thienyl)-isoquinoline

Properties: Orange oil

Mass analysis (m/z, FAB): 288 ($M^+$+1)

Nuclear magnetic resonance spectrum ($CDCl_3$, TMS internal standard)

δ: 1.2–1.3 (3H, m), 2.7–2.8 (1H, m), 2.9–3.0 (1H, m), 3.1–3.3 (1H, m), 3.9–4.2 (3H, m), 6.2–6.4 (1H, m), 6.83 (1H, s), 6.95–7.26 (6H, m)

REFERENCE EXAMPLE 6

Ethyl 1-(2-furyl)-1,2,3,4-tetrahydro-2-isoquinolinecarboxylate

Starting compound: 1-(2-furyl)-1,2,3,4-tetrahydroisoquinoline

Mass analysis (m/z, EI): 271 ($M^+$)

Nuclear magnetic resonance spectrum ($CDCl_3$, TMS internal standard)

δ: 1.30 (3H, t, J=6.5 Hz), 2.75–2.85 (1H, m), 2.90–3.10 (1H, m), 3.20–3.50 (1H, m), 4.05–4.35 (4H, m), 6.00 (1H, s), 6.20–6.45 (2H, m), 7.15–7.25 (4H, m), 7.33 (1H, s)

REFERENCE EXAMPLE 7

(1R)-Ethyl 1-phenyl-1,2,3,4-tetrahydro-2-isoquinolinecarboxylate

Starting compound: (1R)-1-phenyl-1,2,3,4-tetrahydroisoquinoline

Elemental analysis (for $C_{18}H_{19}NO_2$)

| | C (%) | H (%) | N (%) |
|---|---|---|---|
| Calcd.: | 76.84 | 6.81 | 4.98 |
| Found: | 76.53 | 6.82 | 4.93 |

Specific optical rotation $[\alpha]_D^{25}$: 199.2 (C=1.03, $CHCl_3$)

Mass analysis (m/z, FAB): 282 ($M^+$+1)

REFERENCE EXAMPLE 8

(1S)-Ethyl 1-phenyl-1,2,3,4-tetrahydro-2-isoquinolinecarboxylate

Starting compound: (1S)-1-phenyl-1,2,3,4-tetrahydroisoquinoline

Elemental analysis (for $C_{18}H_{19}NO_2$)

| | C (%) | H (%) | N (%) |
|---|---|---|---|
| Calcd.: | 76.84 | 6.81 | 4.98 |
| Found: | 76.64 | 6.82 | 4.99 |

Specific optical rotation $[\alpha]_D^{25}$: −200.9 (C=1.09, $CHCl_3$)
Mass analysis (m/z, EI): 281 ($M^+$)

REFERENCE EXAMPLE 9

Ethyl 1-(4-chlorophenyl)-1,2,3,4-tetrahydro-2-isoquinolinecarboxylate
Starting compound: 1-(4-chlorophenyl)-1,2,3,4-tetrahydroisoquinoline
Properties: Pale yellow oil
Mass analysis (m/z, EI): 315 ($M^+$)
Nuclear magnetic resonance spectrum ($CDCl_3$, TMS Internal standard)

δ: 1.29 (3H, t, J=7.0 Hz), 2.70–3.52 (3H, m), 4.00–4.30 (1H, m), 4.20 (2H,'q. J 7.0 Hz), 6.35 (1H, s), 7.05–7.35 (8H, m)

REFERENCE EXAMPLE 10

Ethyl 1-(4-fluorophenyl)-1,2,3,4-tetrahydro-2-isoquinolinecarboxylate
Starting compound: 1-(4-fluorophenyl)-1,2,3,4-tetrahydroisoquinoline
Properties: Pale yellow oil
Mass analysis (m/z, FAB): 300 ($M^+$+1)
Nuclear magnetic resonance spectrum ($CDCQ_3$, TMS internal standard)

δ: 1.30 (3H, t, J=8.9 Hz), 2.75 (1H, dd, J=12.5, 3.4 Hz), 2.9–3.1 (1H, m), 3.1–3.3 (1H, m), 4.0–4.3 (3H, m), 6.2–6.4 (1H, m), 6.93–7.03 (3H, m), 7.16–7.24 (5H, m).

REFERENCE EXAMPLE 11

Ethyl 1,2,3,4-tetrahydro-1-(4-tolyl)-2-isoquinolinecarboxylate
Starting compound: 1,2,3,4-tetrahydro-1-(4-tolyl) isoquinoline
Mass analysis (m/z, EI): 295 ($M^+$)
Nuclear magnetic resonance spectrum ($CDCl_3$, TMS internal standard)

δ: 1.20–1.35 (3H, m), 2.30 (3H, s), 2.70–2.80 (1H, m), 2.90–3.10 (1H, m), 3.23 (1H, t, J=10.0 Hz), 3.95–4.30 (3H, m), 6.29, 6.41 (1H, brs×2), 7.00–7.25 (8H, m).

REFERENCE EXAMPLE 12

Ethyl 1-benzyl-1,2,3,4-tetrahydro-2-isoquinolinecarboxylate
Starting compound: 1-benzyl-1,2,3,4-tetrahydroisoquinoline
Properties: Pale yellow oil
Mass analysis (m/z, FAB): 296 ($M^+$+1)
Nuclear magnetic resonance spectrum ($CDCl_3$, TMS internal standard)

δ: 1.02, 1.23 (3H, t×2, J=7.1 Hz), 2.63–3.20 (4H, m), 3.30–3.50 (1H, m), 3.75–4.25 (3H, m), 5.27, 5.38 (1H, t×2, J=6.8 Hz), 6.85–7.28 (9H, m).

REFERENCE EXAMPLE 13

Ethyl 1-cyclohexyl-1,2,3,4-tetrahydro-2-isoquinolinecarboxylate
Starting compound: 1-cyclohexyl-1,2,3,4-tetrahydroisoquinoline Properties: yellow oil Mass analysis (m/z, FAB): 288 ($M^+$+1)

Nuclear magnetic resonance spectrum ($CDCl_3$, TMS internal standard)

δ: 0.70–2.00 (11H, m), 1.26 (3H, t, J=7.3 Hz), 2.89 (2H, t, J=7.1 Hz), 3.25–4.20 (2H, m), 4.14 (2H, q, J=7.1 Hz), 4.65–4.95 (1H, m), 7.00–7.30 (4H, m).

REFERENCE EXAMPLE 14

Ethyl 1-(3-furyl)-1,2,3,4-tetrahydro-2-isoquinolinecarboxylate

Starting compound: 1-(3-furyl)-1,2,3,4-tetrahydroisoquinoline

Properties: yellow oil

Mass analysis (m/z, EI): 271 ($M^+$)

Nuclear magnetic resonance spectrum ($CDCl_3$, TMS internal standard)

δ: 1.31 (3H, t, J=7.0 Hz), 2.55–3.40 (3H, m), 3.90–4.30 (1H, m), 4.22 (2H, q, J=7.0 Hz), 6.20–6.45 (2H, m), 6.95–7.40 (6H, m).

The chemical structural formulas of the compounds obtained in Reference Examples 1–14 are shown in the following Tables 1–2.

TABLE 1

| Reference Example No. | Structural Formula |
|---|---|
| 1 | 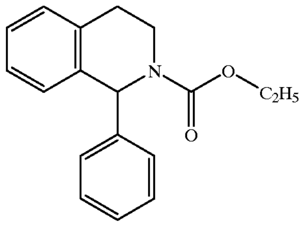 |
| 2 | 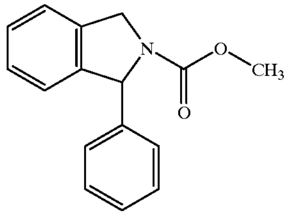 |
| 3 | 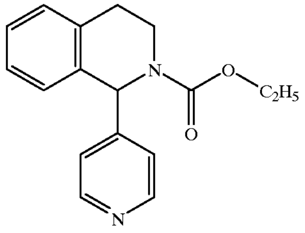 |

TABLE 1-continued
| Reference Example No. | Structural Formula |
|---|---|
| 4 | 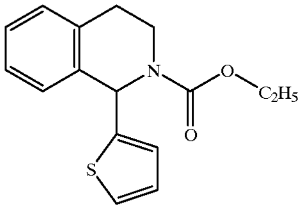 |
| 5 | 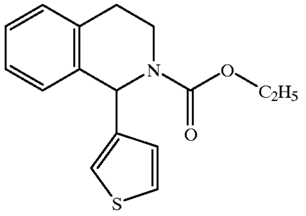 |
| 6 | 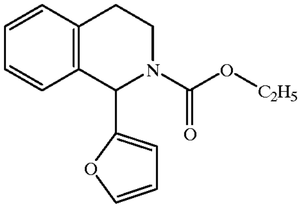 |
| 7 | 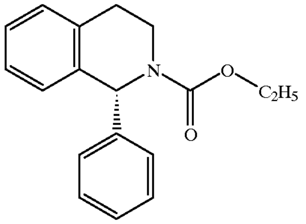 |
| 8 | 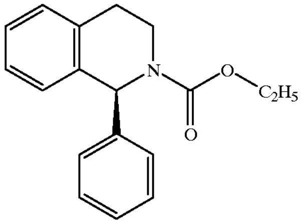 |
| 9 | 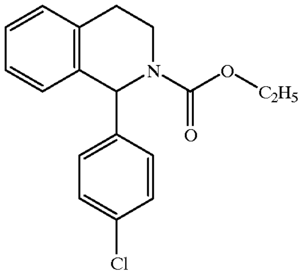 |
TABLE 1-continued
| Reference Example No. | Structural Formula |
|---|---|
| 10 | 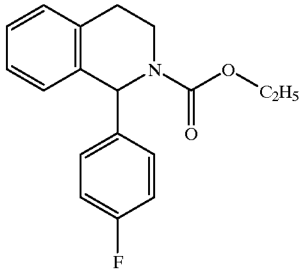 |
TABLE 2
| Reference Example No. | Structural Formula |
|---|---|
| 11 | 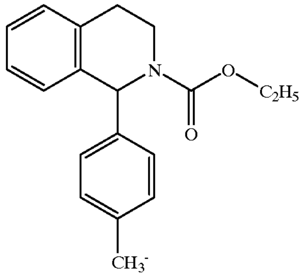 |
| 12 | 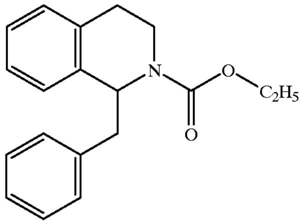 |
| 13 | 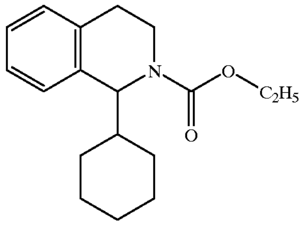 |
| 14 | 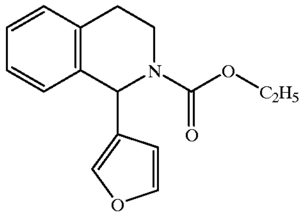 |

EXAMPLE 1

To a 30 ml toluene solution containing 0.70 g of ethyl 1-phenyl-1,2,3,4-tetrahydroisoquinoline-2-carboxylate and 0.41 g of 3-quinuclidinol, 0.03 g of sodium hydride (60%) was added. The resulting mixture was stirred at 140° C. for 2 days while removing the ethanol formed. The reaction mixture was cooled to room temperature, brine was added, and the mixture was extracted with ethyl acetate. The organic layer was dried over anhydrous sodium sulfate and the solvent was removed under reduced pressure. The resulting residue was purified by silica gel column chromatography (chloroform:methanol=10:1→chloroform:methanol:28% aqueous ammonia=10:1:0.1), thereby 0.11 g of 3-quinuclidinyl 1-phenyl-1,2,3,4-tetrahydro-2-isoquinolinecarboxylate was obtained as yellow oil. The resulting oil was dissolved in 10 ml of ethanol, followed by the addition of 27 mg of oxalic acid. Then, the solvent was removed under reduced pressure. The resulting solid was recrystallized from isopropanol and isopropyl ether, thereby 0.08 g of 3-quinuclidinyl 1-phenyl-1,2,3,4-tetrahydro-2-isoquinolinecarboxylate monooxalate was obtained as colorless crystals.

Melting point: 122–124° C. (i-PrOH-i-$Pr_2O$)

Elemental analysis (for $C_{25}H_{28}N_2O_6.0.75H_2O$)

| | C (%) | H (%) | N (%) |
|---|---|---|---|
| Calcd.: | 64.43 | 6.38 | 6.01 |
| Found: | 64.25 | 6.15 | 5.88 |

In a similar manner to Example 1, the compound of Example 2 was obtained.

EXAMPLE 2

3-Quinuclidinyl 1-phenyl-2-isoindolinecarboxylate monohydrochloride

Starting compound: methyl 1-phenyl-2-isoindolinecarboxylate

Melting point: 164–165° C. (EtOH-$Et_2O$)

Elemental analysis (for $C_{22}H_{25}N_2O_2Cl.1.75H_2O$)

| | C (%) | H (%) | N (%) | Cl (%) |
|---|---|---|---|---|
| Calcd.: | 63.45 | 6.90 | 6.73 | 8.51 |
| Found: | 63.54 | 6.59 | 6.76 | 8.12 |

EXAMPLE 3

To a 50 ml toluene suspension containing 720 mg of ethyl 1-(4-pyridyl)-1,2,3,4-tetrahydro-2-isoquinolinecarboxylate and 973 mg of 3-quinuclidinol, 102 mg of sodium hydride (60%) was added at room temperature. The resulting mixture was heated under reflux for 5 hours and 40 minutes while the resulting ethanol was removed together with toluene. The reaction mixture was cooled to room temperature, followed by addition of 20 ml of water. The resulting mixture was extracted with chloroform. The organic layer was washed with water and brine, dried over anhydrous sodium sulfate and then concentrated under reduced pressure. The resulting residue was purified by silica gel column chromatography (chloroform:methanol:28% aqueous ammonia=100:2:1), thereby 827 mg of 3-quinuclidinyl 1-(4-pyridyl)-1,2,3,4-tetrahydro-2-isoquinolinecarboxylate were obtained as yellow oil. The resulting oil was dissolved in 5 ml of ethyl acetate, 2 ml of a 4N hydrogen chloride in ethyl acetate solution was added. The solvent was then removed under reduced pressure. Ethanol and ether were added to the residue, and the crude crystals thus obtained was recrystallized from ethanol and ether, thereby 402 mg of 3-quinuclidinyl 1-(4-pyridyl)-1,2,3,4-tetrahydro-2-isoquinolinecarboxylate dihydrochloride was obtained as pale yellow crystals.

Melting point: 167–169° C. (EtOH—$Et_2O$)

Elemental analysis (for $C_{22}H_{27}N_3O_2Cl_22.2H_2O$)

| | C (%) | H (%) | N (%) | Cl (%) |
|---|---|---|---|---|
| Calcd.: | 55.51 | 6.65 | 8.83 | 14.90 |
| Found: | 55.46 | 6.98 | 8.64 | 14.84 |

In a similar manner to Example 3, the compounds of Examples 4 to 6 which will be described below were obtained.

EXAMPLE 4

3-Quinuclidinyl 1,2,3,4-tetrahydro-1-(2-thienyl)-2-isoquinolinecarboxylate monooxalate Starting compound: Ethyl 1,2,3,4-tetrahydro-1-(2-thienyl)-2-isoquinolinecarboxylate Elemental analysis (for $C_{23}H_{26}N_2O_6S.1.3H_2O$)

| | C (%) | H (%) | N (%) | S (%) |
|---|---|---|---|---|
| Calcd.: | 57.32 | 5.98 | 5.81 | 6.65 |
| Found: | 57.62 | 6.00 | 5.84 | 6.27 |

Mass analysis (m/z, FAB): 369 ($M^+$+1)

EXAMPLE 5

(1RS,3'R)-3'-Quinuclidinyl 1,2,3,4-tetrahydro-1-(3-thienyl)-2-isoquinolinecarboxylate Starting compounds: ethyl 1,2,3,4-tetrahydro-1-(3-thienyl)-2-isoquinolinecarboxylate, (3R)-3-quinuclidinol Properties: Brown oil Elemental analysis (for $C_{21}H_{24}N_2O_2S.0.3H_2O$)

| | C (%) | H (%) | N (%) | S (%) |
|---|---|---|---|---|
| Calcd.: | 67.46 | 6.63 | 7.49 | 8.58 |
| Found: | 67.35 | 6.76 | 7.21 | 8.46 |

Mass analysis (m/z, FAB): 369 ($M^+$+1)

EXAMPLE 6

3-Quinuclidinyl 1-(2-furyl)-1,2,3,4-tetrahydro-2-isoquinolinecarboxylate

Starting compound: ethyl 1-(2-furyl)-1,2,3,4-tetrahydro-2-isoquinolinecarboxylate Properties: Pale yellow oil Elemental analysis (for $C_{21}H_{24}N_2O_3.0.5H_2O$)

| | C (%) | H (%) | N (%) |
|---|---|---|---|
| Calcd.: | 69.79 | 6.97 | 7.75 |
| Found: | 70.03 | 7.05 | 7.44 |

Mass analysis (m/z, FAB): 353 ($M^{+}$+1)

EXAMPLE 7

To a 30 ml pyridine solution containing 2.09 g of (1R)-1-phenyl-1,2,3,4-tetrahydroisoquinoline, 2.26 g of 3-quinuclidinyl chloroformate monohydrochloride was added at room temperature, followed by stirring at 80° C. for 4 hours. Then, 0.12 g of 3-quinuclidinyl chloroformate monohydrochloride, followed by stirring at 80° C. for 4 hours. Then, 1.01 g of 3-quinuclidinyl chloroformate monohydrochloride was added, and the mixture was stirring at 80° C. for 25 hours. The reaction mixture was concentrated under reduced pressure. Water was added to the residue, followed by washing with ethyl acetate twice. The resulting aqueous layer was adjusted to pH 9 with saturated sodium hydrogencarbonate aqueous solution, followed by extraction with ethyl acetate. After the organic layer was dried over anhydrous sodium sulfate, the solvent was removed under reduced pressure, thereby 3.02 g of (1R,3'RS)-3'-quinuclidinyl 1-phenyl-1,2,3,4-tetrahydro-2-isoquinolinecarboxylate was obtained as yellow oil.

Mass analysis (m/z, FAB): 363 ($M^{+}$+1)

Nuclear magnetic resonance spectrum (DMSO-$d_6$, TMS internal standard)

δ: 1.20–2.00 (5H, m), 2.40–2.95 (6H, m), 3.00–3.60 (3H, m), 3.80–3.95 (1H, m), 4.55–4.70 (1H, m), 6.25 (1H, brs), 7.05–7.35 (10H, m).

EXAMPLE 8

To a 120 ml toluene suspension containing 12.0 g of (1R)-ethyl 1-phenyl-1,2,3,4-tetrahydro-2-isoquinolinecarboxylate and 16.27 g of (3R)-3-quinuclidinol, 1.69 g of sodium hydride (60%) was added at room temperature. The resulting mixture was heated for 3 hours while the resulting ethanol was removed together with toluene. The reaction mixture was cooled to room temperature, and 50 ml of brine was added, followed by extraction with ethyl acetate. The organic layer was washed with water and then extracted with 20% hydrochloric acid. The resulting aqueous layer was adjusted to pH 9 to 10 by adding a IN aqueous solution of sodium hydroxide, followed by extraction with ethyl acetate. The organic layer was washed with brine, dried over anhydrous sodium sulfate and then concentrated under reduced pressure. The residue was dissolved in 140 ml of ethanol, and 10 ml of a 4N hydrogen chloride in ethyl acetate solution was added to the resulting solution. The solvent was then removed under reduced pressure. Acetonitrile and ether were added to the residue, and the resulting crude crystals were recrystallized from acetonitrile and ether, thereby 10.1 g of (1R,3'R)-3'-quinuclidinyl 1-phenyl-1,2,3,4-tetrahydro-2-isoquinolinecarboxylate monohydrochloride was obtained as colorless crystals.

Melting point: 212–214° C. ($CH_3CN$—$Et_2O$)

Elemental analysis (for $C_{23}H_{27}N_2O_2Cl$)

| | C (%) | H (%) | N (%) | Cl (%) |
|---|---|---|---|---|
| Calcd.: | 69.25 | 6.82 | 7.02 | 8.89 |
| Found: | 69.24 | 6.89 | 7.03 | 8.97 |

Specific optical rotation $[\alpha]_D^{25}$: 98.1 (C=1.00, EtOH)

In a similar manner to Example 8, the compounds of the following Examples 9 to 16 were obtained.

EXAMPLE 9

(1S,3'S)-3'-quinuclidinyl 1-phenyl-1,2,3,4-tetrahydro-2-isoquinolinecarboxylate monohydrochloride Starting compounds: (1S)-ethyl 1-phenyl-1,2,3,4-tetrahydro-2-isoquinolinecarboxylate, (3S)-3-quinuclidinol Melting point: 211–212° C. (EtOH—$Et_2O$)

Elemental analysis (for $C_{23}H_{27}N_2O_2Cl.0.25H_2O$)

| | C (%) | H (%) | N (%) | Cl (%) |
|---|---|---|---|---|
| Calcd.: | 68.48 | 6.87 | 6.94 | 8.79 |
| Found: | 68.32 | 6.75 | 6.94 | 8.94 |

Specific optical rotation $[\alpha]_D^{25}$: −97.4 (C=50, EtOH)

EXAMPLE 10

(1S,3'R)-3'-quinuclidinyl 1-phenyl-1,2,3,4-tetrahydro-2-isoquinolinecarboxylate monohydrochloride Starting compounds: (1S)-ethyl 1-phenyl-1,2,3,4-tetrahydro-2-isoquinolinecarboxylate, (3R)-3-quinuclidinol Melting point: 195–196° C. (EtOH—$Et_2O$)

Elemental analysis (for $C_{23}H_{27}N_2O_2Cl.0.25H_2O$)

| | C (%) | H (%) | N (%) | Cl (%) |
|---|---|---|---|---|
| Calcd.: | 68.48 | 6.87 | 6.94 | 8.79 |
| Found: | 68.73 | 6.88 | 6.95 | 8.70 |

Specific optical rotation $[\alpha]_D^{25}$: −151.2 (C=0.50, EtOH)

EXAMPLE 11

(1R,3'S)-3'-quinuclidinyl 1-phenyl-1,2,3,4-tetrahydro-2-isoquinolinecarboxylate monohydrochloride Starting compounds: (1R)-ethyl 1-phenyl-1,2,3,4-tetrahydro-2-isoquinolinecarboxylate, (3S)-3-quinuclidinol Melting point: 194–195° C. ($CH_3CN$—$Et_2O$)

Elemental analysis (for $C_{23}H_{27}N_2O_2Cl$)

| | C (%) | H (%) | N (%) | Cl (%) |
|---|---|---|---|---|
| Calcd.: | 69.25 | 6.82 | 7.02 | 8.89 |
| Found: | 69.08 | 6.71 | 6.99 | 8.91 |

Specific optical rotation $[\alpha]_D^{25}$: 163.2 (C=0.50, EtOH)

EXAMPLE 12

3-quinuclidinyl 1-(4-chlorophenyl)-1,2,3,4-tetrahydro-2-isoquinolinecarboxylate monofumarate Starting compounds: 1-(4-chlorophenyl)-1,2,3,4-tetrahydro-2-isoquinolinecarboxylate Melting point: 164–166° C. (EtOH—$Et_2O$)
Elemental analysis (for $C_{27}H_{29}N_2O_6Cl.0.5H_2O$)

| | C (%) | H (%) | N (%) | Cl (%) |
|---|---|---|---|---|
| Calcd.: | 62.13 | 5.79 | 5.37 | 6.79 |
| Found: | 62.19 | 5.68 | 5.23 | 6.49 |

EXAMPLE 13

(1RS,3'R)-3'-quinuclidinyl 1-(4-fluorophenyl)-1,2,3,4-tetrahydro-2-isoquinoli-necarboxylate
Starting compounds: ethyl 1-(4-fluorophenyl)-1,2,3,4-tetrahydro-2-isoquinolinecarboxylate, (3R)-3-quinuclidinol
Properties: colorless oil
Elemental analysis (for $C_{23}H_{25}N_2O_2F.0.1H_2O$)

| | C (%) | H (%) | N (%) | F (%) |
|---|---|---|---|---|
| Calcd.: | 72.27 | 6.64 | 7.33 | 4.97 |
| Found: | 72.05 | 6.63 | 7.15 | 4.99 |

Mass analysis (m/z, FAB): 381 ($M^+$+1)

EXAMPLE 14

3-quinuclidinyl 1,2,3,4-tetrahydro-1-(4-tolyl)-2-isoquinolinecarboxylate
Starting compounds: ethyl 1,2,3,4-tetrahydro-1-(4-tolyl)-2-isoquinolinecarboxylate
Properties: colorless oil
Elemental analysis (for $C_{24}H_{28}N_2O_2.0.8H_2O$)

| | C (%) | H (%) | N (%) |
|---|---|---|---|
| Calcd.: | 73.74 | 7.63 | 7.17 |
| Found: | 73.96 | 7.50 | 6.95 |

Mass analysis (m/z, FAB): 377 ($M^+$+1)

EXAMPLE 15

3-Quinuclidinyl 1-benzyl-1,2,3,4-tetrahydro-2-isoquinolinecarboxylate
Starting compound: ethyl 1-benzyl-1,2,3,4-tetrahydro-2-isoquinolinecarboxylate
Properties: pale yellow oil
Elemental analysis (for $C_{24}H_{28}N_2O_2.0.5H_2O$)

| | C (%) | H (%) | N (%) |
|---|---|---|---|
| Calcd.: | 74.78 | 7.58 | 7.26 |
| Found: | 74.95 | 7.83 | 7.18 |

Mass analysis (m/z, FAB): 377 ($M^+$+1)

EXAMPLE 16

3-Quinuclidinyl 1-cyclohexyl-1,2,3,4-tetrahydro-2-isoquinolinecarboxylate
Starting compounds: ethyl 1-cyclohexyl-1,2,3,4-tetrahydro-2-isoquinolinecarboxylate
Properties: pale yellow amorphous
Elemental analysis (for $C_{23}H_{32}N_2O_2.0.3H_2O$)

| | C (%) | H (%) | N (%) |
|---|---|---|---|
| Calcd.: | 73.88 | 8.79 | 7.49 |
| Found: | 73.76 | 8.75 | 7.37 |

Mass analysis (m/z, FAB): 369 ($M^+$+1)

EXAMPLE 17

In 12 ml of dichloromethane, 1.20 g of (1R,3'R)-3'-quinuclidinyl 1-phenyl-1,2,3,4-tetrahydro-2-isoquinolinecarboxylate was dissolved, 0.33 g of sodium hydrogencarbonate and 0.79 g of m-chloroperbenzoic acid (80%) were added under ice-cooling, followed by stirring at room temperature for one hour. Water was added to the reaction mixture and then the mixture was extracted with dichloromethane. The organic layer was washed with an aqueous solution of sodium thiosulfate and then dried over anhydrous magnesium sulfate. The solvent was then removed under reduced-pressure, and the residue was purified by silica gel column chromatography (chloroform:methanol=20:1), thereby 0.43 g of (1'R,3R)-3-[[(1'-phenyl-1',2',3',4'-tetrahydro-2'-isoquinolyl)carbonyl]oxy]quinuclidine 1-oxide was obtained.
Properties: white amorphous
Mass analysis (m/z, FAB): 379 ($M^+$+1)
Nuclear magnetic resonance spectrum ($CDCl_3$, TMS internal standard)

δ: 1.85–2.15 (3H, m), 2.15–2.35 (2H, m), 2.75–2.90 (1H, m), 2.90–2.95 (1H, m), 3.20–3.50 (6H, m), 3.70–3.80 (1H, m), 3.85–4.10 (iH, m), 5.14 (1H, brs), 6.14, 6.43 (1H, brs×2), 7.05–7.40 (9H, m).

EXAMPLE 18

To a 8 ml 2-butanone solution containing 1.04 g of (1R,3'R)-3'-quinuclidinyl 1-phenyl-1,2,3,4-tetrahydro-2-isoquinolinecarboxylate, 0.18 ml of methyl iodide was added, followed by stirring at 55° C. for 40 minutes. After air cooling, the crystals precipitated were collected by filtration and then washed successively with 2-butanone and diethyl ether, thereby 0.93 g of (1'R,3R)-1-methyl-3-[[(1'-phenyl-1',2',3',4'-tetrahydro-2'-isoquinolyl)carbonyl]oxy]quinuclidinium iodide was obtained as colorless crystals.
Melting point: 202–203° C.. (2-butanone)
Elemental analysis (for $C_{24}H_{29}N_2O_2I$)

| | C (%) | H (%) | N (%) | I (%) |
|---|---|---|---|---|
| Calcd.: | 57.15 | 5.79 | 5.55 | 25.16 |
| Found: | 57.17 | 5.71 | 5.51 | 25.15 |

In a similar manner to Example 8, the compound of the following Example 19 was obtained.

EXAMPLE 19

(1RS,3'R)-3'-quinuclidinyl 1-(3-furyl)-1,2,3,4-tetrahydro-2-isoquinolinecarboxylate
Starting compound: ethyl 1-(3-furyl)-1,2,3,4-tetrahydro-2-isoquinolinecarboxylate
Properties: yellow oil Elemental analysis (for $C_{21}H_{24}N_2O_3.0.3H_2O$)
| | C (%) | H (%) | N (%) |
|---|---|---|---|
| Calcd.: | 70.49 | 6.93 | 7.83 |
| Found: | 70.35 | 6.83 | 7.63 |
Mass analysis (m/z, EI): 352 ($M^+$)
The chemical structural formulas of the compounds obtained in Examples 1–19 are shown below in Tables 3–5.
TABLE 3
| Example No. | Structural Formula |
|---|---|
| 1 | 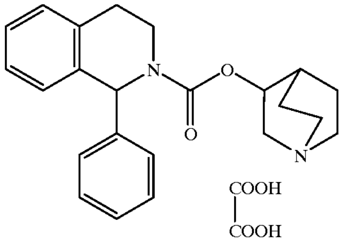 |
| 2 | 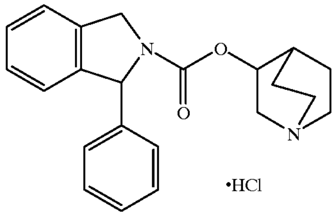 •HCl |
| 3 | 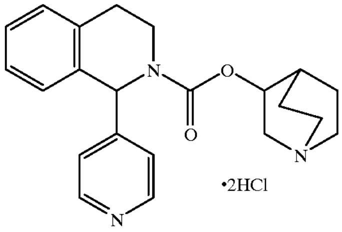 •2HCl |
| 4 | 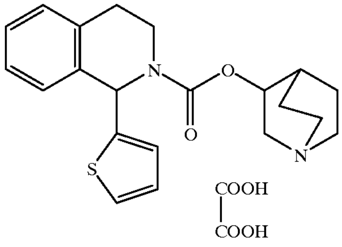 |
| 5 | 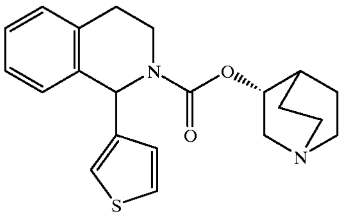 |
TABLE 3-continued
| Example No. | Structural Formula |
|---|---|
| 6 | 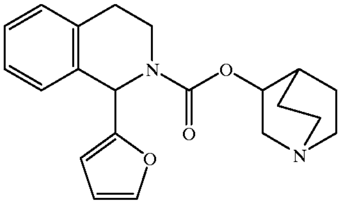 |
| 7 | 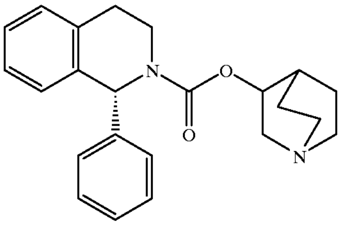 |
| 8 | 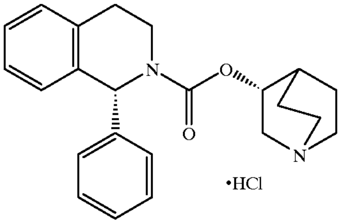 •HCl |
| 9 | 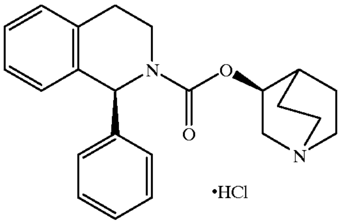 •HCl |
| 10 | 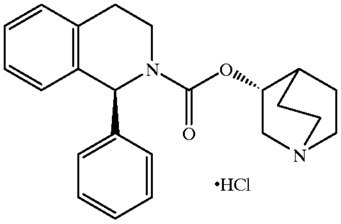 •HCl |

TABLE 4
| Example No. | Structural Formula |
|---|---|
| 11 | 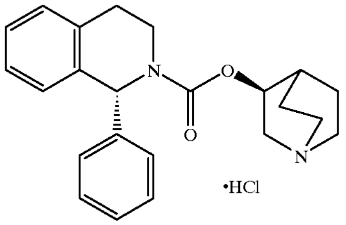 |
| 12 | 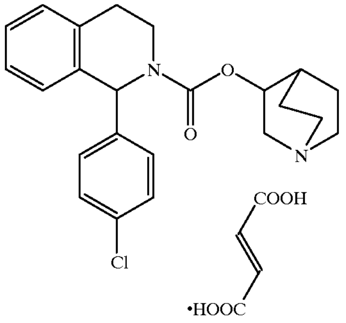 |
| 13 | 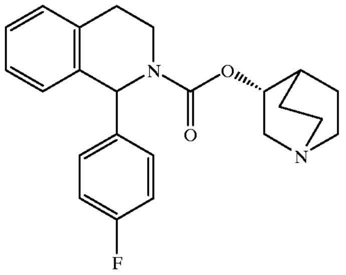 |
| 14 | 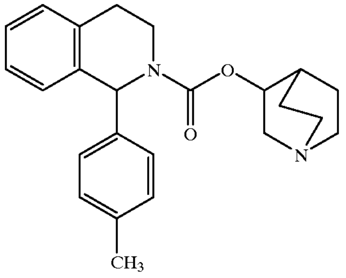 |
| 15 | 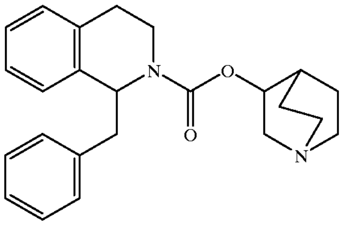 |
TABLE 4-continued
| Example No. | Structural Formula |
|---|---|
| 16 | 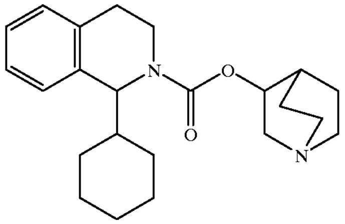 |
| 17 | 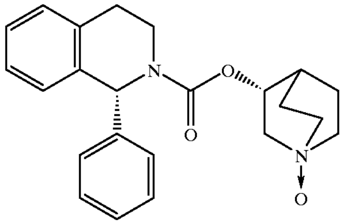 |
| 18 | 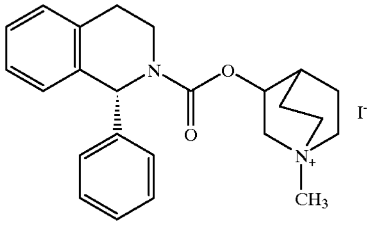 |
TABLE 5
| Example No. | Structural Formula |
|---|---|
| 19 | 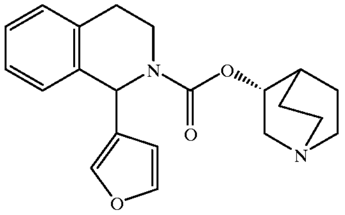 |
Each of the above-described compounds in Examples 3–6, 12–14, 16 and 19 can be obtained as an optical resolved form as shown in the following Tables 6–8 using an optically resolved intermediate in a similar manner to Examples 8–11.
TABLE 6
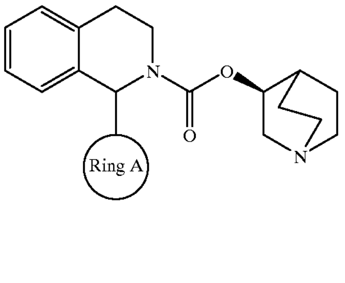

| Example No. | Ring A | Example No. | Ring A |
|---|---|---|---|
| 3-(a) | 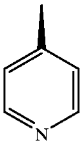 | 3-(b) | 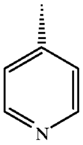 |
| 4-(a) | 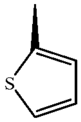 | 4-(b) | 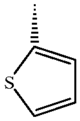 |
| 5-(a) | 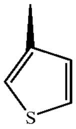 | 5-(b) | 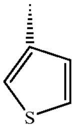 |
| 6-(a) | 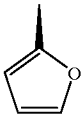 | 6-(a) | 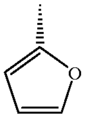 |
| 12-(a) | 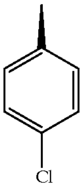 | 12-(b) | 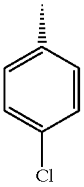 |
| 13-(a) | 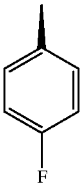 | 13-(b) | 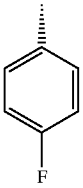 |
| 14-(a) | 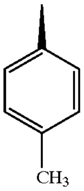 | 14-(b) | 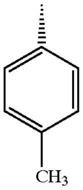 |
| 16-(a) | 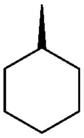 | 16-(b) | 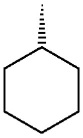 |
TABLE 7
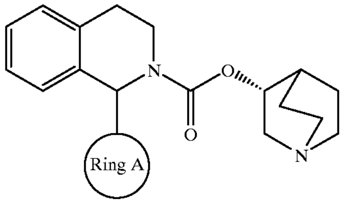
| Example No. | Ring A | Example No. | Ring A |
|---|---|---|---|
| 3-(c) | 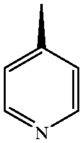 | 3-(d) | 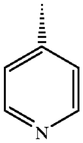 |
| 4-(c) | 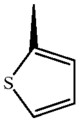 | 4-(d) | 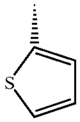 |
| 5-(c) | 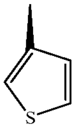 | 5-(d) | 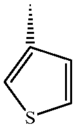 |
| 6-(c) | 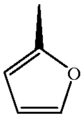 | 6-(d) | 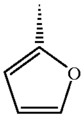 |
| 12-(c) | 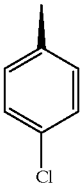 | 12-(d) | 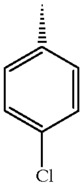 |
| 13-(c) | 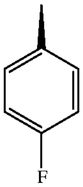 | 13-(d) | 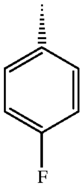 |
| 14-(c) | 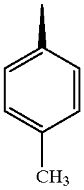 | 14-(d) | 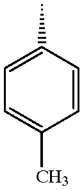 |

TABLE 7-continued

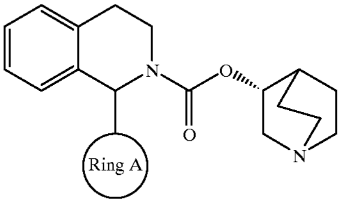

| Example No. | Ring A | Example No. | Ring A |
|---|---|---|---|
| 16-(c) | 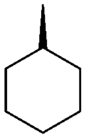 | 16-(d) | 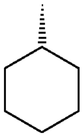 |

TABLE 8

| Example No. | Structural Formula |
|---|---|
| 19-(a) | 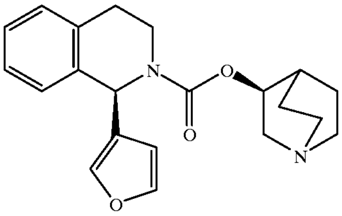 |
| 19-(b) | 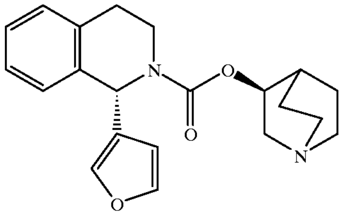 |
| 19-(c) | 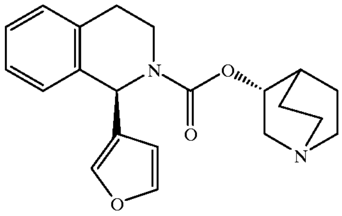 |
| 19-(d) | 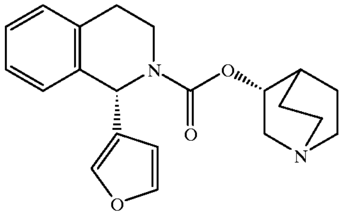 |

The other compounds embraced by the present invention will be shown in Tables 9–33. They can be synthesized by any one of the above-described preparation processes, processes described in Examples or processes known to those skilled in the art and do not require any particular experiment. Incidentally, these compounds are described as a racemic compound, but optical active substances based on an asymmetric carbon is also included.

TABLE 9

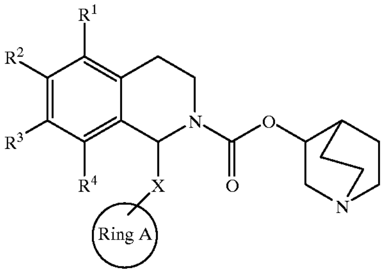

| Compound No. | $R^1$ | $R^2$ | $R^3$ | $R^4$ | X | Ring A |
|---|---|---|---|---|---|---|
| A-1 | Cl | H | H | H | — | 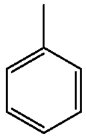 |
| A-2 | H | H | Cl | H | — | 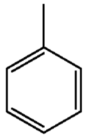 |
| A-3 | Cl | H | Cl | H | — | 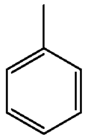 |
| A-4 | F | H | H | H | — | 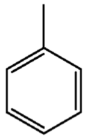 |
| A-5 | H | H | F | H | — | 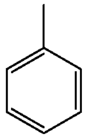 |
| A-6 | Br | H | H | H | — | 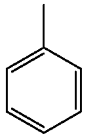 |
| A-7 | H | H | Br | H | — | 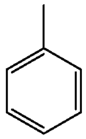 |

TABLE 9-continued
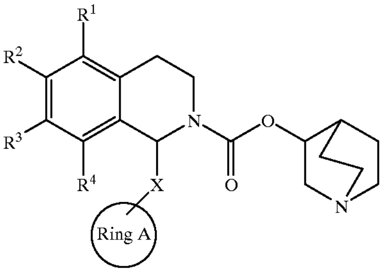
| Compound No. | $R^1$ | $R^2$ | $R^3$ | $R^4$ | X | Ring A |
|---|---|---|---|---|---|---|
| A-8 | Cl | H | Br | H | — | 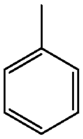 |
| A-9 | $CH_3$ | H | H | H | — | 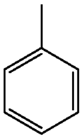 |
TABLE 10
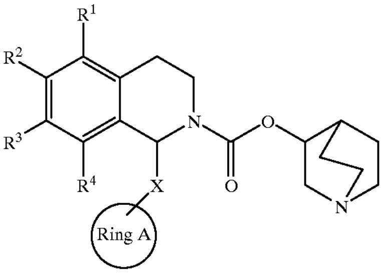
| Compound No. | $R^1$ | $R^2$ | $R^3$ | $R^4$ | X | Ring A |
|---|---|---|---|---|---|---|
| A-10 | $C_2H_5$ | H | H | H | — | 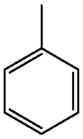 |
| A-11 | n-$C_3H_7$ | H | H | H | — | 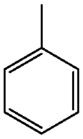 |
| A-12 | i-$C_3H_7$ | H | H | H | — | 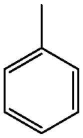 |
TABLE 10-continued
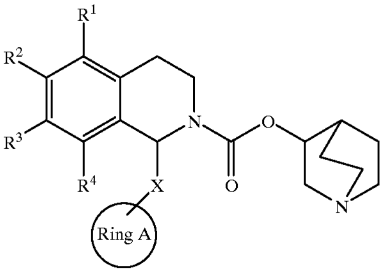
| Compound No. | $R^1$ | $R^2$ | $R^3$ | $R^4$ | X | Ring A |
|---|---|---|---|---|---|---|
| A-13 | H | $CH_3$ | H | H | — | 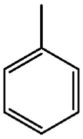 |
| A-14 | H | $C_2H_5$ | H | H | — | 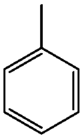 |
| A-15 | H | H | $CH_3$ | H | — | 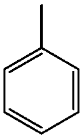 |
| A-16 | H | H | $C_2H_5$ | H | — | 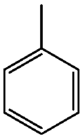 |
| A-17 | $CH_3$ | H | $CH_3$ | H | — | 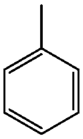 |
| A-18 | H | $CH_3$ | $CH_3$ | H | — | 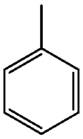 |

TABLE 11
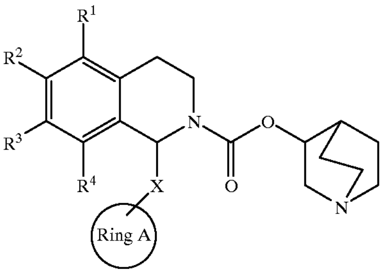
| Compound No. | $R^1$ | $R^2$ | $R^3$ | $R^4$ | X | Ring A |
|---|---|---|---|---|---|---|
| A-19 | $CH_3$ | H | $CH_3$ | $CH_3$ | — | 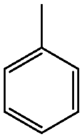 |
| A-20 | Cl | H | H | H | — | 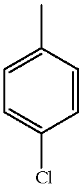 |
| A-21 | H | H | Cl | H | — | 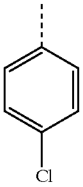 |
| A-22 | H | H | Cl | H | — | 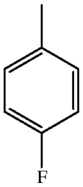 |
| A-23 | H | H | Cl | H | — | 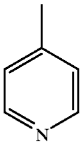 |
| A-24 | H | H | Cl | H | — | 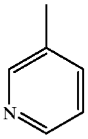 |
TABLE 11-continued
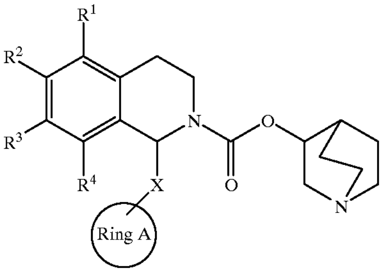
| Compound No. | $R^1$ | $R^2$ | $R^3$ | $R^4$ | X | Ring A |
|---|---|---|---|---|---|---|
| A-25 | H | H | Cl | H | — | 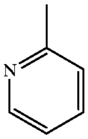 |
TABLE 12
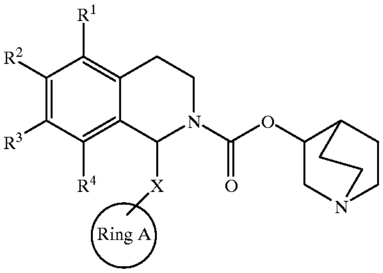
| Compound No. | $R^1$ | $R^2$ | $R^3$ | $R^4$ | X | Ring A |
|---|---|---|---|---|---|---|
| A-26 | H | H | $CH_3$ | H | — | 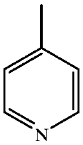 |
| A-27 | Cl | H | H | H | — | 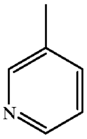 |
| A-28 | H | $CH_3$ | H | H | — | 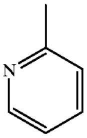 |
| A-29 | Cl | H | H | H | — | 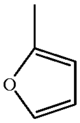 |

TABLE 12-continued
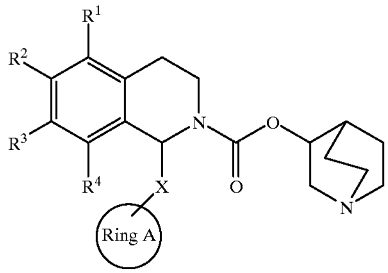
| Compound No. | $R^1$ | $R^2$ | $R^3$ | $R^4$ | X | Ring A |
|---|---|---|---|---|---|---|
| A-30 | Cl | H | H | H | — | 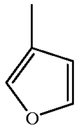 |
| A-31 | H | H | Cl | H | — | 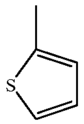 |
| A-32 | H | H | Cl | H | — | 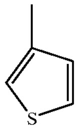 |
| A-33 | H | $OCH_3$ | $OCH_3$ | H | — | 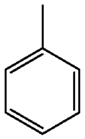 |
| A-34 | H | —$OCH_2O$— | | H | — | 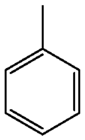 |
TABLE 13
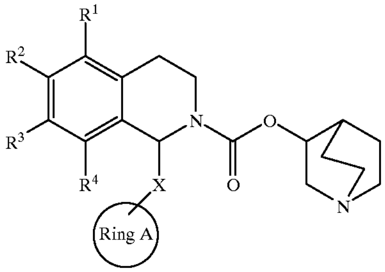
| Compound No. | $R^1$ | $R^2$ | $R^3$ | $R^4$ | X | Ring A |
|---|---|---|---|---|---|---|
| A-35 | H | H | H | H | $CH_2$ | 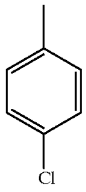 |
| A-36 | H | H | H | H | $CH_2$ | 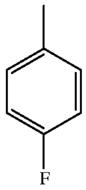 |
| A-37 | H | H | H | H | $CH_2$ | 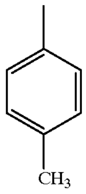 |
| A-38 | H | H | H | H | $CH_2$ | 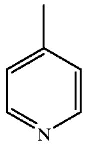 |
| A-39 | H | H | H | H | $CH_2$ | 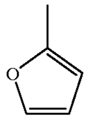 |
| A-40 | Cl | H | H | H | $CH_2$ | 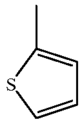 |
| A-41 | Cl | H | H | H | $CH_2$ | 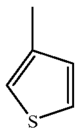 |

TABLE 13-continued
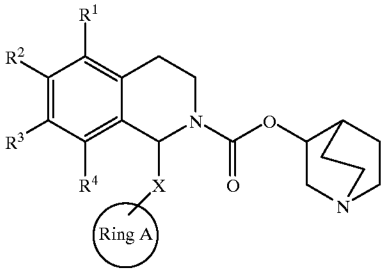
| Compound No. | $R^1$ | $R^2$ | $R^3$ | $R^4$ | X | Ring A |
|---|---|---|---|---|---|---|
| A-42 | Cl | H | H | H | $CH_2$ | 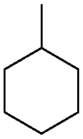 |
TABLE 14
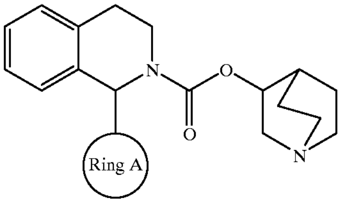
| Compound No. | Ring A |
|---|---|
| B-1 | 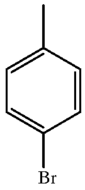 |
| B-2 | 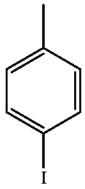 |
| B-3 | 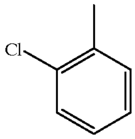 |
TABLE 14-continued
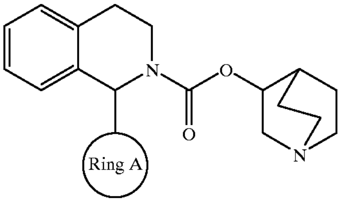
| Compound No. | Ring A |
|---|---|
| B-4 | 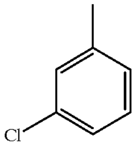 |
| B-5 | 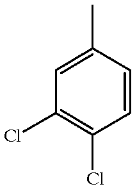 |
| B-6 | 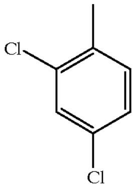 |
| B-7 | 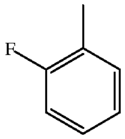 |
| B-8 | 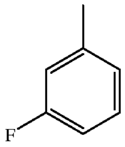 |
| B-9 | 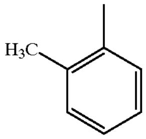 |
| B-10 | 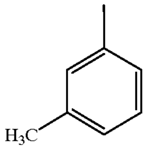 |

TABLE 14-continued
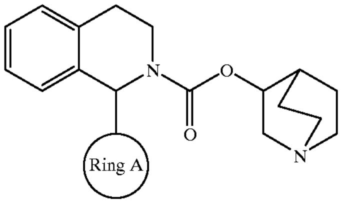
| Compound No. | Ring A |
|---|---|
| B-11 | 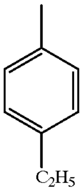 |
| B-12 | 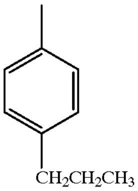 |
TABLE 15
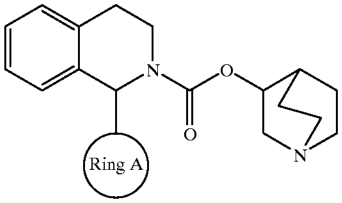
| Compound No. | Ring A |
|---|---|
| B-13 | 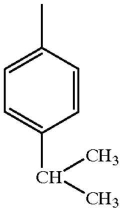 |
| B-14 | 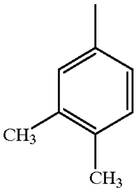 |
TABLE 15-continued
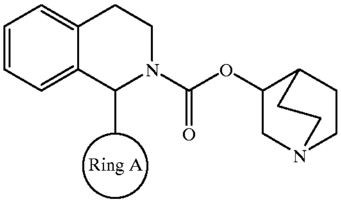
| Compound No. | Ring A |
|---|---|
| B-15 | 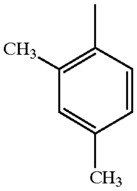 |
| B-16 | 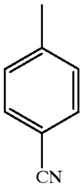 |
| B-17 | 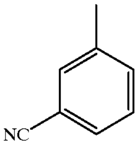 |
| B-18 | 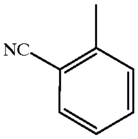 |
| B-19 | 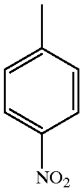 |
| B-20 | 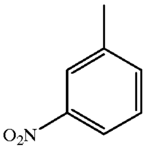 |
| B-21 | 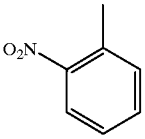 |

TABLE 15-continued
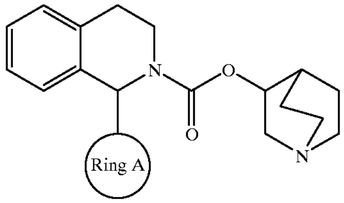
| Compound No. | Ring A |
|---|---|
| B-22 | 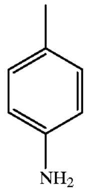 |
| B-23 | 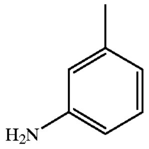 |
| B-24 | 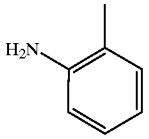 |
TABLE 16
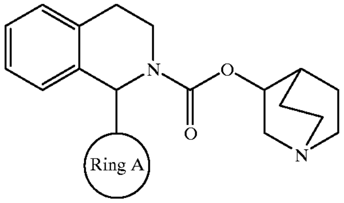
| Compound No. | Ring A |
|---|---|
| B-25 | 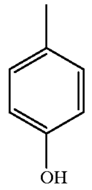 |
| B-26 | 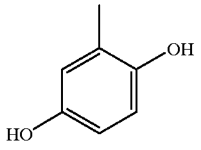 |
TABLE 16-continued
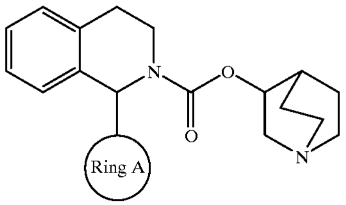
| Compound No. | Ring A |
|---|---|
| B-27 | 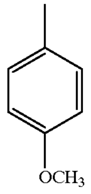 |
| B-28 | 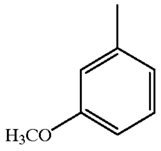 |
| B-29 | 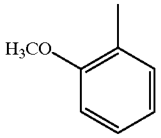 |
| B-30 | 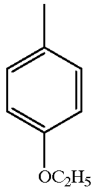 |
| B-31 | 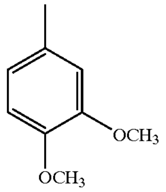 |
| B-32 | 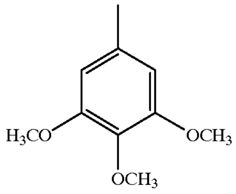 |

TABLE 16-continued
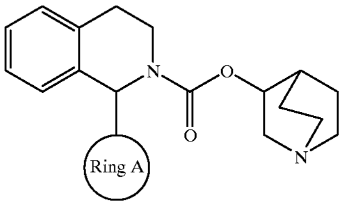
| Compound No. | Ring A |
|---|---|
| B-33 | 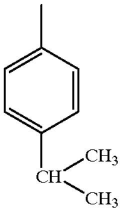 |
| B-34 | 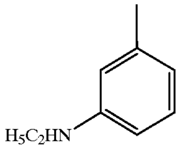 |
| B-35 | 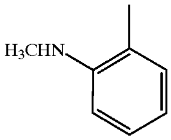 |
| B-36 | 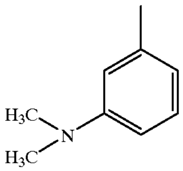 |
TABLE 17
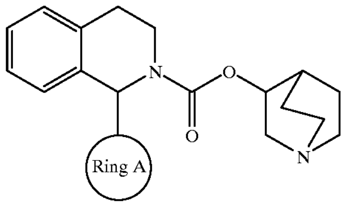
| Compound No. | Ring A |
|---|---|
| B-37 | 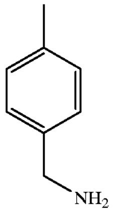 |
| B-38 | 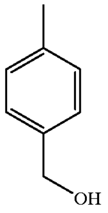 |
| B-39 | 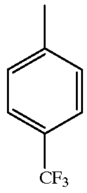 |
| B-40 | 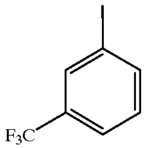 |
| B-41 | 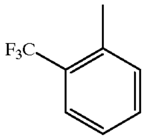 |
| B-42 | 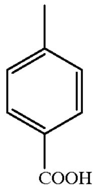 |

TABLE 17-continued
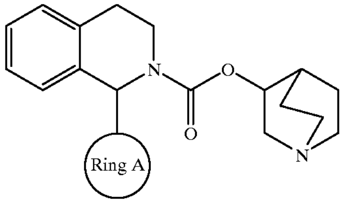
| Compound No. | Ring A |
| --- | --- |
| B-43 | 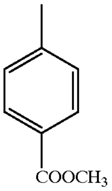 |
| B-44 | 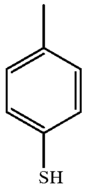 |
| B-45 | 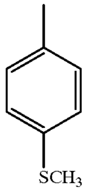 |
| B-46 | 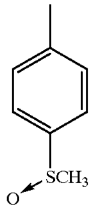 |
| B-47 | 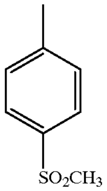 |
| B-48 | 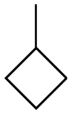 |
TABLE 18
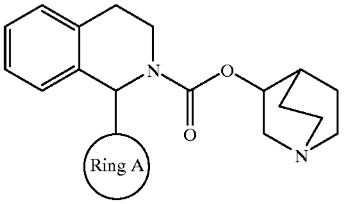
| Compound No. | Ring A |
| --- | --- |
| B-49 | 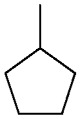 |
| B-50 | 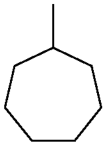 |
| B-51 | 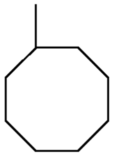 |
| B-52 | 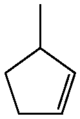 |
| B-53 | 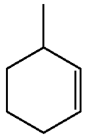 |
| B-54 | 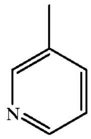 |
| B-55 | 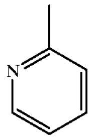 |
| B-56 | 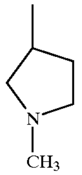 |

TABLE 18-continued
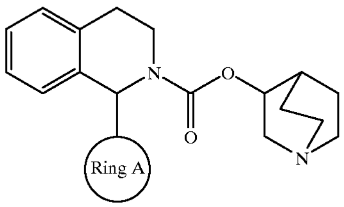
| Compound No. | Ring A |
|---|---|
| B-57 | 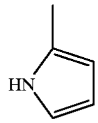 |
| B-58 | 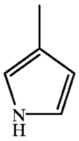 |
| B-59 | 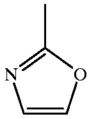 |
| B-60 | 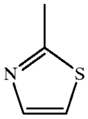 |
TABLE 19
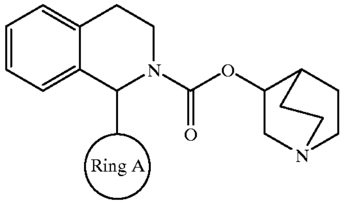
| Compound No. | Ring A |
|---|---|
| B-61 | 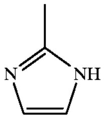 |
| B-62 | 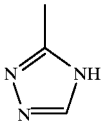 |
TABLE 19-continued
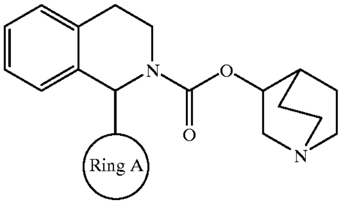
| Compound No. | Ring A |
|---|---|
| B-63 | 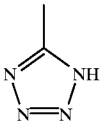 |
| B-64 | 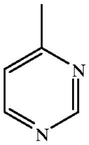 |
| B-65 | 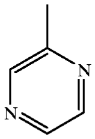 |
| B-66 | 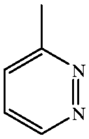 |
| B-67 | 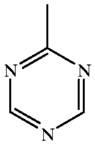 |
| B-68 | 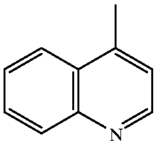 |
| B-69 | 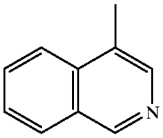 |
| B-70 | 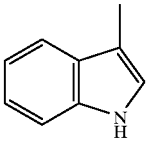 |

TABLE 19-continued
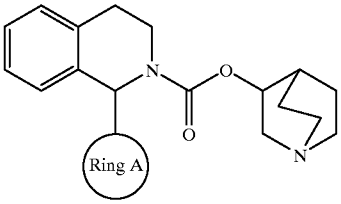
| Compound No. | Ring A |
|---|---|
| B-71 | 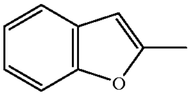 |
| B-72 | 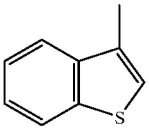 |
TABLE 20
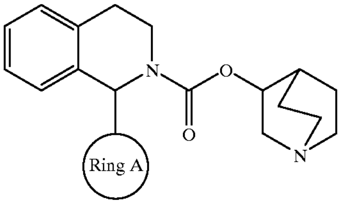
| Compound No. | Ring A |
|---|---|
| B-73 | 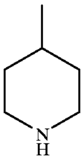 |
| B-74 | 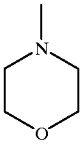 |
| B-75 | 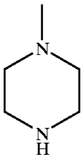 |
TABLE 21
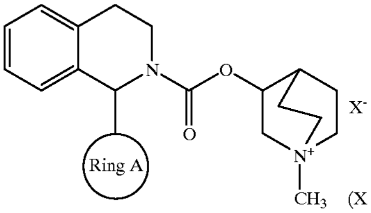
(X = Br. I)
| Compound No. | Ring A |
|---|---|
| B-76 | 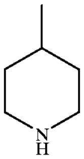 |
| B-77 | 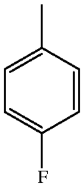 |
| B-78 | 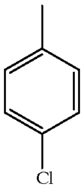 |
| B-79 | 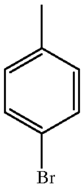 |
| B-80 | 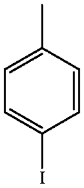 |
| B-81 | 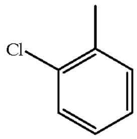 |

TABLE 21-continued
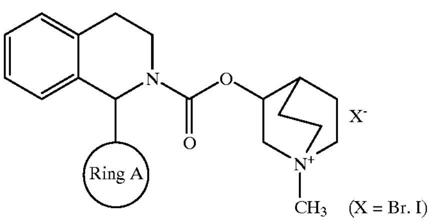
| Compound No. | Ring A |
|---|---|
| B-82 | 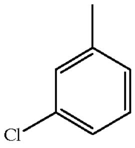 |
| B-83 | 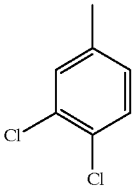 |
| B-84 | 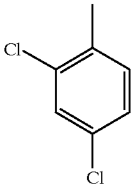 |
| B-85 | 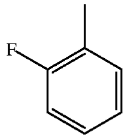 |
| B-86 | 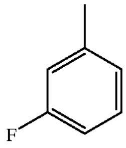 |
| B-87 | 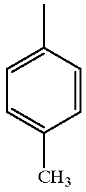 |
TABLE 22
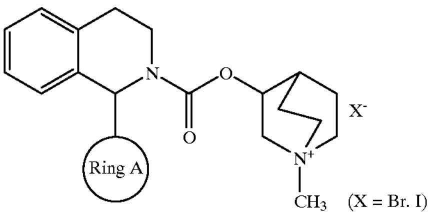
| Compound No. | Ring A |
|---|---|
| B-88 | 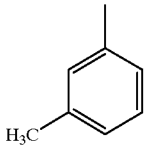 |
| B-89 | 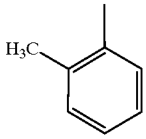 |
| B-90 | 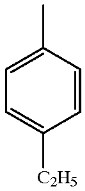 |
| B-91 | 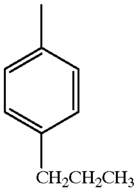 |
| B-92 | 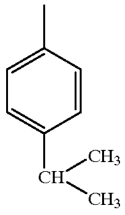 |
| B-93 | 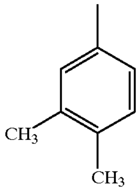 |

TABLE 22-continued
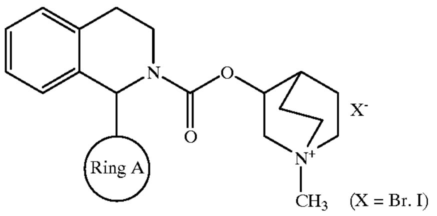
| Compound No. | Ring A |
|---|---|
| B-94 | 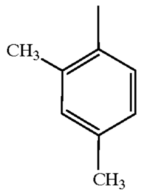 |
| B-95 | 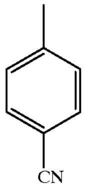 |
| B-96 | 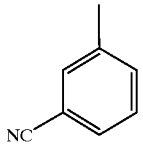 |
| B-97 | 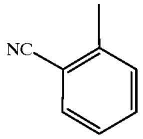 |
| B-98 | 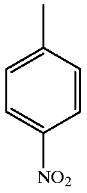 |
| B-99 | 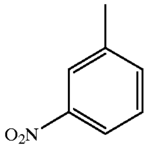 |
TABLE 23
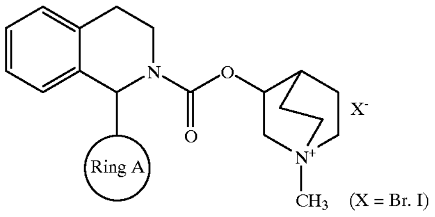
| Compound No. | Ring A |
|---|---|
| B-100 | 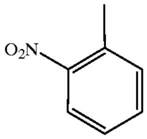 |
| B-101 | 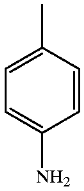 |
| B-102 | 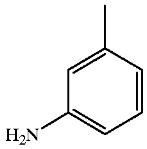 |
| B-103 | 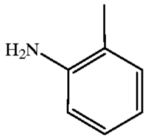 |
| B-104 | 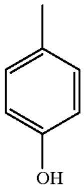 |
| B-105 | 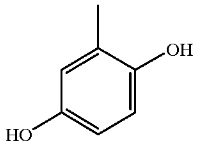 |
| B-106 | 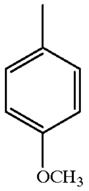 |

TABLE 23-continued
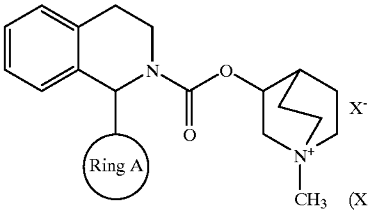
(X = Br. I)
| Compound No. | Ring A |
|---|---|
| B-107 | 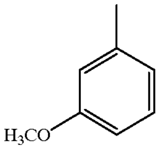 |
| B-108 | 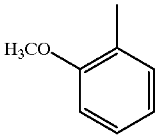 |
| B-109 | 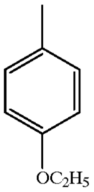 |
| B-110 | 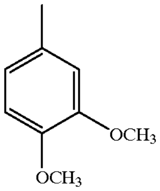 |
| B-111 | 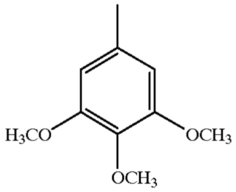 |
TABLE 24
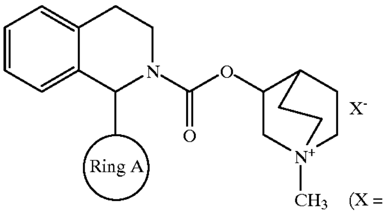
(X = Br. I)
| Compound No. | Ring A |
|---|---|
| B-112 | 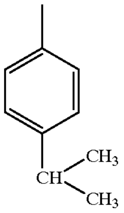 |
| B-113 | 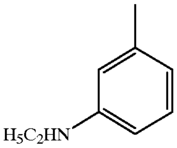 |
| B-114 | 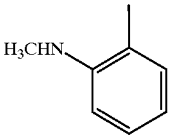 |
| B-115 | 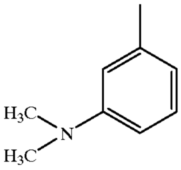 |
| B-116 | 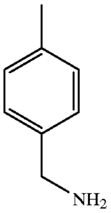 |
| B-117 | 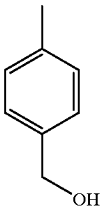 |

TABLE 24-continued
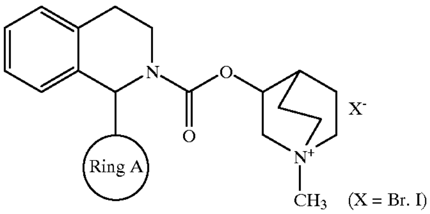
| Compound No. | Ring A |
|---|---|
| B-118 | 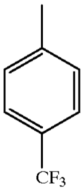 |
| B-119 | 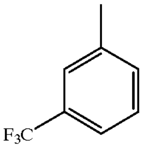 |
| B-120 | 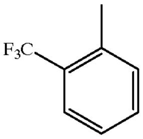 |
| B-121 | 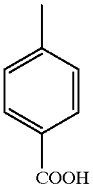 |
| B-122 | 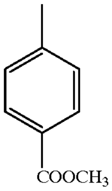 |
| B-123 | 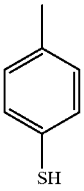 |
TABLE 25
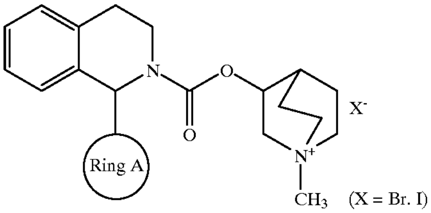
| Compound No. | Ring A |
|---|---|
| B-124 | 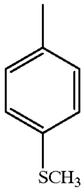 |
| B-125 | 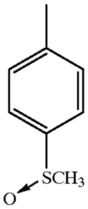 |
| B-126 | 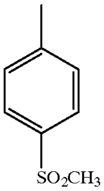 |
| B-127 | 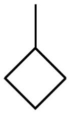 |
| B-128 | 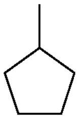 |
| B-129 | 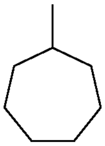 |
| B-130 | 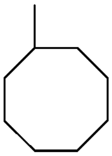 |

TABLE 25-continued
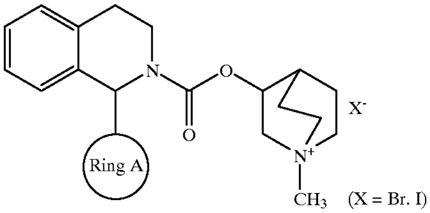
| Compound No. | Ring A |
| --- | --- |
| B-131 | 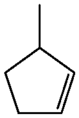 |
| B-132 | 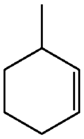 |
| B-133 | 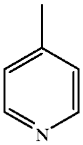 |
| B-134 | 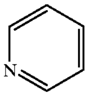 |
| B-135 | 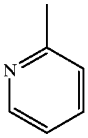 |
TABLE 26
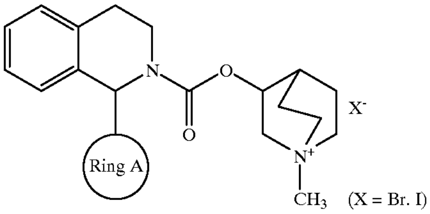
| Compound No. | Ring A |
| --- | --- |
| B-136 | 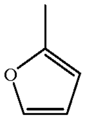 |
TABLE 26-continued
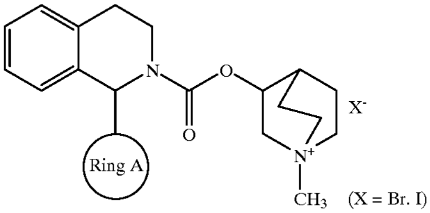
| Compound No. | Ring A |
| --- | --- |
| B-137 | 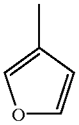 |
| B-138 | 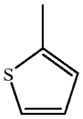 |
| B-139 | 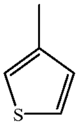 |
| B-140 | 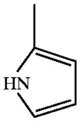 |
| B-141 | 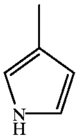 |
| B-142 | 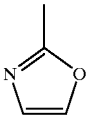 |
| B-143 | 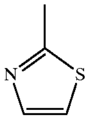 |
| B-144 | 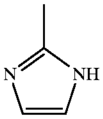 |
| B-145 | 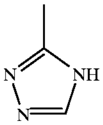 |

TABLE 26-continued
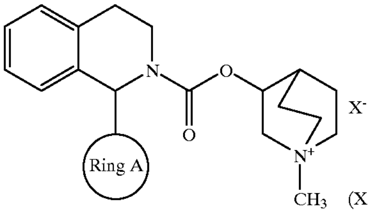
(X = Br. I)
| Compound No. | Ring A |
|---|---|
| B-146 | 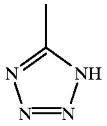 |
| B-147 | 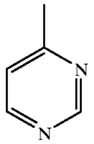 |
TABLE 27
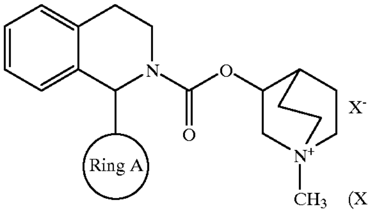
(X = Br. I)
| Compound No. | Ring A |
|---|---|
| B-148 | 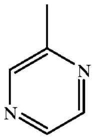 |
| B-149 | 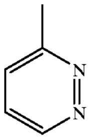 |
| B-150 | 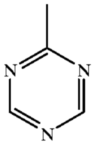 |
TABLE 27-continued
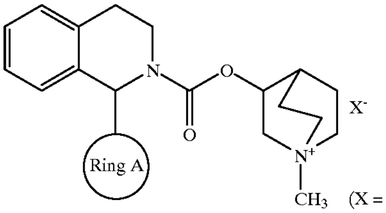
(X = Br. I)
| Compound No. | Ring A |
|---|---|
| B-151 | 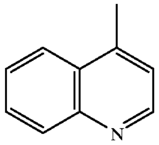 |
| B-152 | 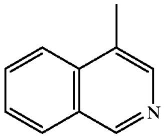 |
| B-153 | 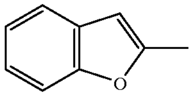 |
| B-154 | 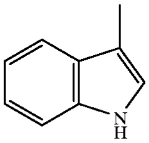 |
| B-155 | 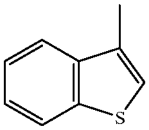 |
| B-156 | 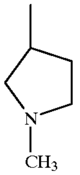 |
TABLE 28
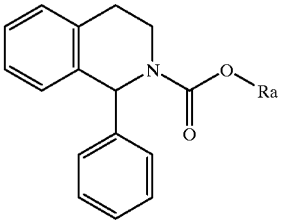

| Compound No. | Ring A |
|---|---|
| B-157 | 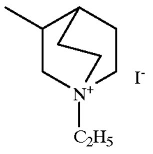 |
| B-158 | 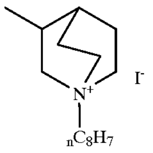 |
TABLE 29
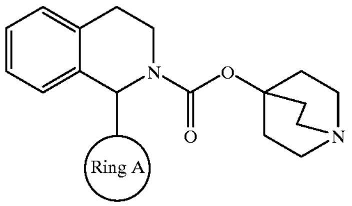
| Compound No. | Ring A |
|---|---|
| B-159 | 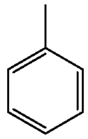 |
| B-160 | 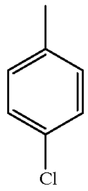 |
| B-161 | 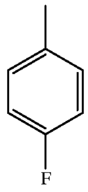 |
| B-162 | 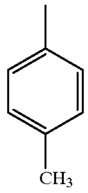 |
TABLE 29-continued
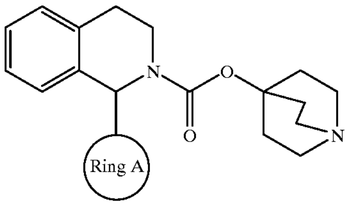
| Compound No. | Ring A |
|---|---|
| B-163 | 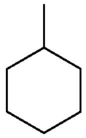 |
| B-164 | 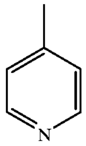 |
| B-165 | 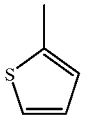 |
| B-166 | 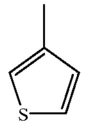 |
| B-167 | 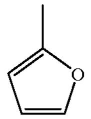 |
| B-168 | 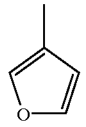 |

TABLE 30
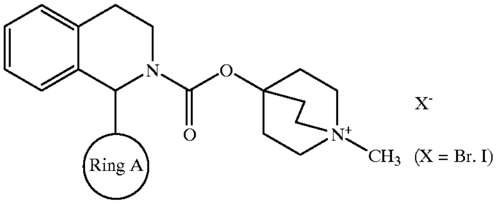
| Compound No. | Ring A |
|---|---|
| B-169 | 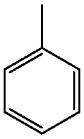 |
| B-170 | 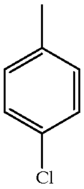 |
| B-171 | 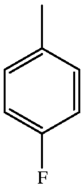 |
| B-172 | 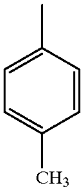 |
| B-173 | 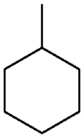 |
| B-174 | 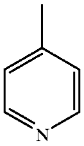 |
| B-175 | 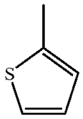 |
TABLE 30-continued
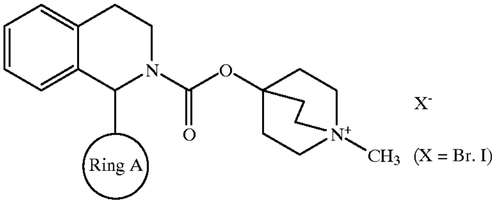
| Compound No. | Ring A |
|---|---|
| B-176 | 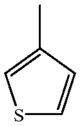 |
| B-177 | 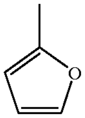 |
| B-178 | 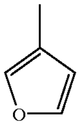 |
TABLE 31
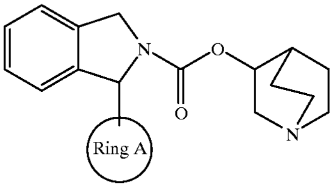
| Compound No. | Ring A |
|---|---|
| B-179 | 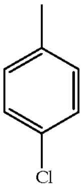 |
| B-180 | 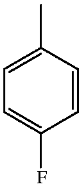 |

TABLE 31-continued
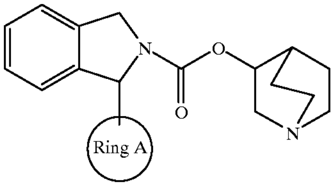
| Compound No. | Ring A |
|---|---|
| B-181 | 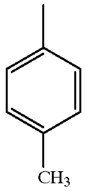 |
| B-182 | 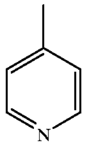 |
| B-183 | 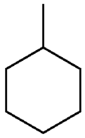 |
| B-184 | 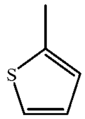 |
| B-185 | 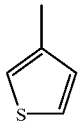 |
| B-186 | 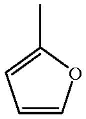 |
| B-187 | 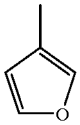 |
TABLE 32
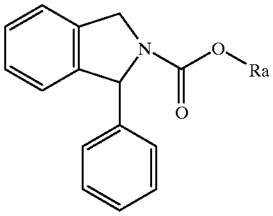
| Compound No. | $R_a$ |
|---|---|
| B-188 | 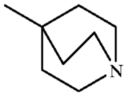 |
| B-189 | 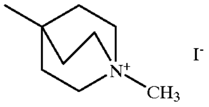 |
| B-190 | 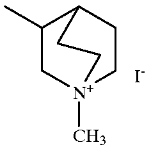 |
TABLE 33
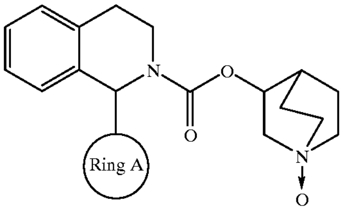
| Compound No. | Ring A |
|---|---|
| B-191 | 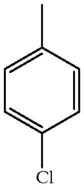 |
| B-192 | 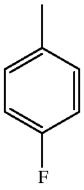 |

TABLE 33-continued

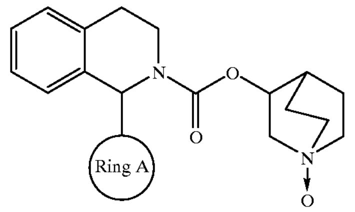

| Compound No. | Ring A |
|---|---|
| B-193 | 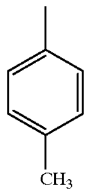 |
| B-194 | 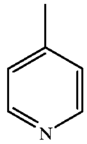 |
| B-195 | 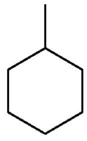 |
| B-196 | 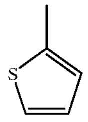 |
| B-197 | 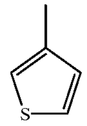 |
| B-198 | 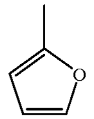 |
| B-199 | 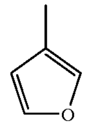 |

What is claimed is:

1. A quinuclidine derivative represented by the following formula (I):

(I)

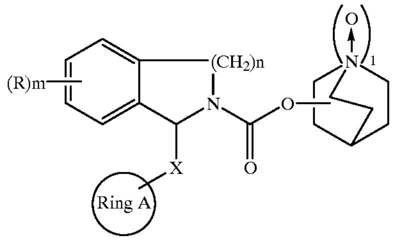

wherein the symbols in the formula have the following meaning:

Ring A: a pyridyl group, a furyl group or a thienyl group;

X: a single bond or a methylene group;

R: a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group or a lower alkyl group which may be substituted by a halogen atom, a hydroxyl group, a lower alkoxy group, an amino group or a mono- or di-lower alkylamino group;

l: 0 or 1;

m: 0 or an integer of 1 to 3; and n: 2, or a salt thereof or a quaternary ammonium salt thereof.

2. The quinuclidine derivative, a salt thereof, or a quaternary ammonium salt thereof according to claim 1, wherein R represents a halogen atom, a lower alkyl group, a hydroxyl group, a lower alkoxy group, a nitro group, a cyano group, an amino group or a mono- or di-lower alkylamino group.

3. The quinuclidine derivative, a salt thereof, or a quaternary ammonium salt thereof according to claim 1, wherein m is 0.

4. The quinuclidine derivative, a salt thereof, or a quaternary ammonium salt thereof according to any one of claims 2 to 3, wherein X represents a single bond.

5. A quinuclidine derivative, a salt thereof, or a quaternary ammonium salt thereof according to claim 1, which is selected from the group consisting of 3-quinuclidinyl 1-phenyl-1,2,3,4-tetrahydro-2-isoquinolinecarboxylate, 3-quinuclidinyl 1-(4-pyridyl)-1,2,3,4-tetrahydro-2-isoquinolinecarboxylate, 3-quinuclidinyl 1,2,3,4-tetrahydro-1-(2-thienyl)-2-isoquinolinecarboxylate, 3-quinuclidinyl 1,2,3,4-tetrahydro-1-(3-thienyl)-2-isoquinolinecarboxylate, 3-quinuclidinyl 1-(2-furyl)-1,2,3,4-tetrahydro-2-isoquinolinecarboxylate, 3-quinuclidinyl 1-(4-chlorophenyl)-1,2,3,4-tetrahydro-2-isoquinolinecarboxylate, 3-quinuclidinyl 1-(4-fluorophenyl)-1,2,3,4-tetrahydro-2-isoquinolinecarboxylate, 3-quinuclidinyl 1,2,3,4-tetrahydro-1-(4-tolyl)2-isoquinolinecarboxylate, 3-quinuclidinyl 1-cyclohexyl-1,2,3,4-tetrahydro-2-isoquinolinecarboxylate, and 3-quinuclidinyl 1-(3-furyl)-1,2,3,4-tetrahydro-2-isoquinoline carboxylate.

6. A pharmaceutical composition which comprises a quinuclidine derivative represented by the following formula (I):

(I)

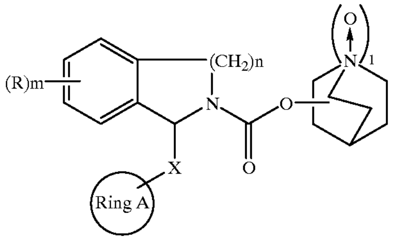

wherein the symbols in the formula have the following meaning:

Ring A: a pyridyl group, a furyl group or a thienyl group;

X: a single bond or a methylene group;

R: a halogen atom, a hydroxyl group, a lower alkoxy group, a carboxyl group, a lower alkoxycarbonyl group, a lower acyl group, a mercapto group, a lower alkylthio group, a sulfonyl group, a lower alkylsulfonyl- group, a sulfinyl group, a lower alkylsulfinyl group, a sulfonamido group, a lower alkanesulfonamido group, a carbamoyl group, a thiocarbamoyl group, a mono- or di-lower alkylcarbamoyl group, a nitro group, a cyano group, an amino group, a mono- or di-lower alkylamino group, a methylenedioxy group, an ethylenedioxy group or a lower alkyl group which may be substituted by a halogen atom, a hydroxyl group, a lower alkoxy group, an amino group or a mono- or di-lower alkylamino group;

l: 0 or 1;

m: 0 or an integer of 1 to 3; and n: 2, or a salt thereof or a quaternary ammonium salt thereof, and a pharmaceutically acceptable carrier.

* * * * *

UNITED STATES PATENT AND TRADEMARK OFFICE

CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 14,
Lines 46 and 48, delete "(1R)" and insert -- (1S) --;
Line 59, delete "C" and insert -- c -- (i.e. small letter).
Lines 64 and 66, delete "(1S)" and insert -- (1R) --.

Column 15.
Line 9, delete "C" and insert -- c -- (i.e. small letter).

Column 17,
Table 1, Example No. 7: the chemical formula should be changed as follows:

Table 1
Example 7

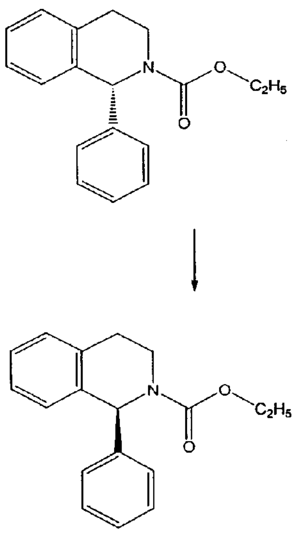

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 17 cont'd,
Table 1, Example No. 8: the chemical formula should be changed as follows:

Table 1
Example 8

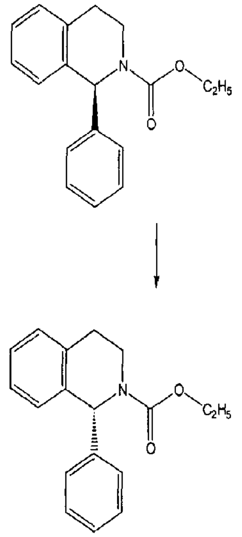

Column 21,
Lines 13 and 42, delete "(1R)" and insert -- (1S) --;
Line 28, delete "(1R,3'RS)" and insert -- (1S,3'RS) --; and
Line 62, delete "(1R,3'R)" and insert -- (1S,3'R) --.

Column 22,
Line 14, delete "(1S,3'S)" and insert -- (1R,3'S) --;
Lines 16 and 32, delete "(1S)" and insert -- (1R) --;
Line 30, delete "(1S,3'R)" and insert -- (1R,3'R) --;
Line 47, delete "(1R,3'S)" and insert -- (1S,3'S) --; and
Line 49, delete "(1R)" and insert -- (1S) --.

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 24,
Line 13, delete "(1R3'R)" and insert -- (1S, 3'R) --;
Line 40, delete "(1R,3'R)" and insert -- (1S,3'R) --; and
Lines 25 and 45, delete "(1'R,3R)" and insert -- (1'S,3R) --.

Column 26,
Table 3, Example No. 7: the chemical formula should be changed as follows:

Table 3
Example 7

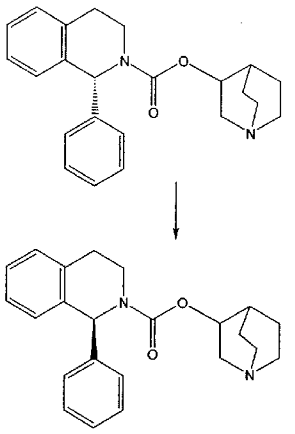

Table 3, Example No. 8: the chemical formula should be changed as follows:

Table 3
Example 8

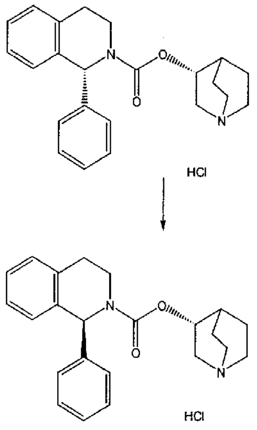

UNITED STATES PATENT AND TRADEMARK OFFICE
CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

<u>Column 26 cont'd,</u>
Table 3, Example No. 9: the chemical formula should be changed as follows:

Table 3
Example 9

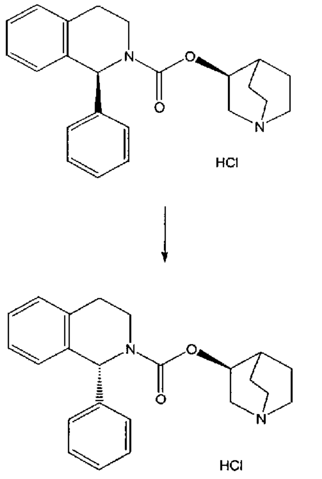

Table 3, Example No. 10: the chemical formula should be changed as follows:

Table 3
Example 10

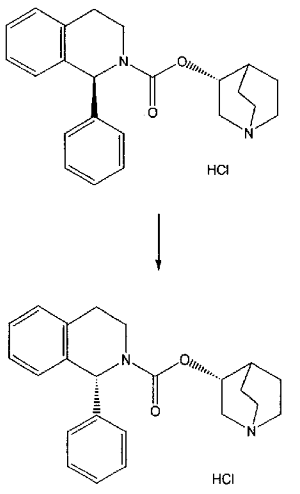

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 27,
Table 4, Example No. 11: the chemical formula should be changed as follows:

Table 4
Example 11

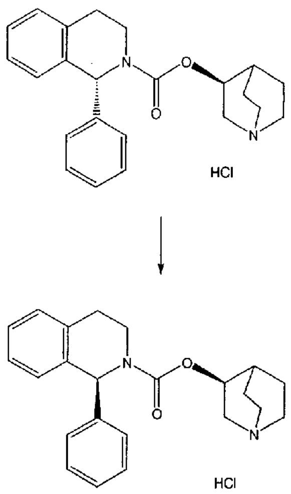

Column 28,
Table 4, Example No. 18: the chemical formula should be change as follows:

Table 4
Example 18

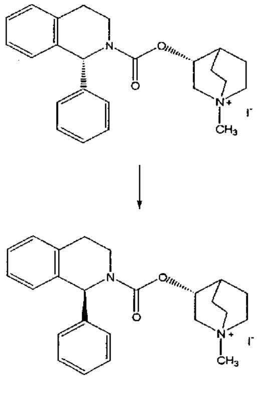

UNITED STATES PATENT AND TRADEMARK OFFICE

CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 61,
Table 25, Compound B-134: the chemical formula should be changed as follows:

Table 25
Compound B-134

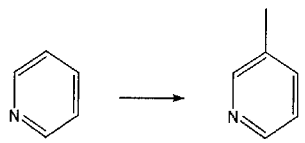

Signed and Sealed this

Twenty-seventh Day of May, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

<u>Column 14,</u>
Lines 46 and 48, delete "(1R)" and insert -- (1S) --;
Line 59, delete "C" and insert -- c -- (i.e. small letter).
Lines 64 and 66, delete "(1S)" and insert -- (1R) --.

<u>Column 15.</u>
Line 9, delete "C" and insert -- c -- (i.e. small letter).

<u>Column 17,</u>
Table 1, Example No. 7: the chemical formula should be changed as follows:

Table 1
Example 7

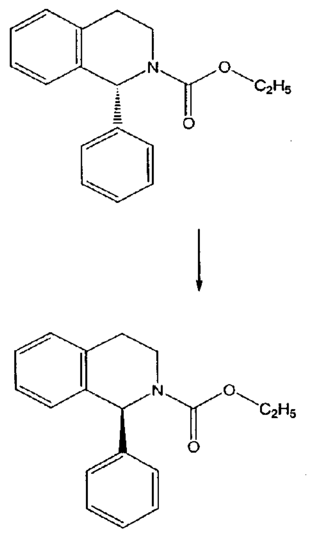

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

<u>Column 17 cont'd,</u>
Table 1, Example No. 8: the chemical formula should be changed as follows:

Table 1
Example 8

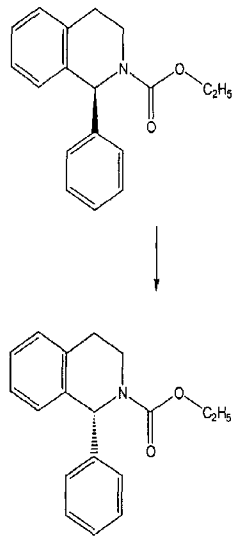

<u>Column 21,</u>
Lines 13 and 42, delete "(1R)" and insert -- (1S) --;
Line 28, delete "(1R,3'RS)" and insert -- (1S,3'RS) --; and
Line 62, delete "(1R,3'R)" and insert -- (1S,3'R) --.

<u>Column 22,</u>
Line 14, delete "(1S,3'S)" and insert -- (1R,3'S) --;
Lines 16 and 32, delete "(1S)" and insert -- (1R) --;
Line 30, delete "(1S,3'R)" and insert -- (1R,3'R) --;
Line 47, delete "(1R,3'S)" and insert -- (1S,3'S) --; and
Line 49, delete "(1R)" and insert -- (1S) --.

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 24,
Line 13, delete "(1R3'R)" and insert -- (1S, 3'R) --;
Line 40, delete "(1R,3'R)" and insert -- (1S,3'R) --; and
Lines 25 and 45, delete "(1'R,3R)" and insert -- (1'S,3R) --.

Column 26,
Table 3, Example No. 7: the chemical formula should be changed as follows:

Table 3
Example 7

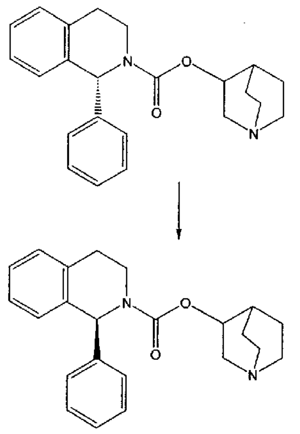

Table 3, Example No. 8: the chemical formula should be changed as follows:

Table 3
Example 8

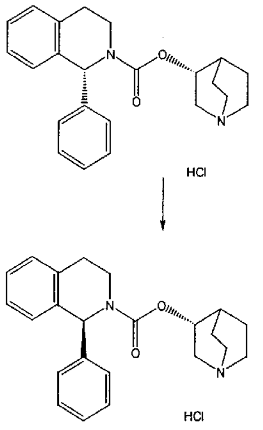

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 26 cont'd,

Table 3, Example No. 9: the chemical formula should be changed as follows:

Table 3
Example 9

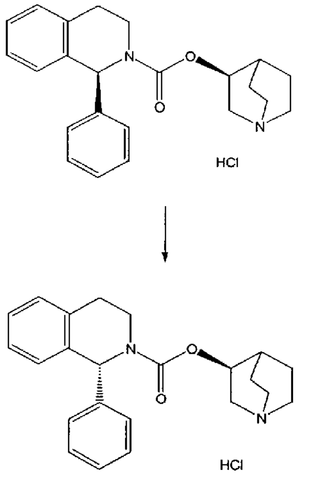

Table 3, Example No. 10: the chemical formula should be changed as follows:

Table 3
Example 10

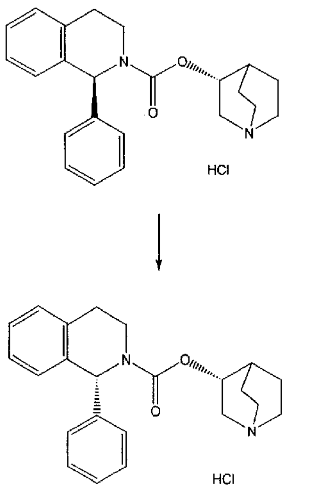

CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 27,
Table 4, Example No. 11: the chemical formula should be changed as follows:

Table 4
Example 11

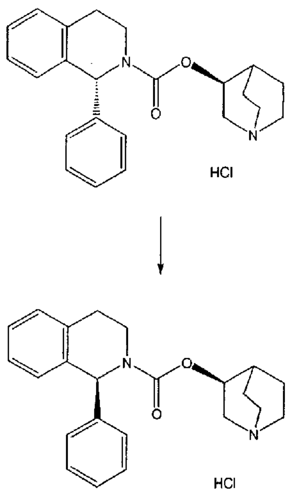

Column 28,
Table 4, Example No. 18: the chemical formula should be change as follows:

Table 4
Example 18

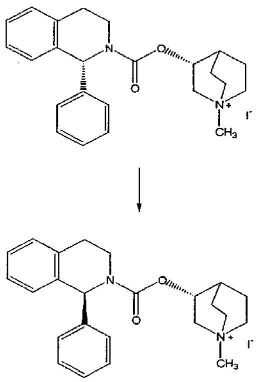

UNITED STATES PATENT AND TRADEMARK OFFICE

CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

Column 61,
Table 25, Compound B-134: the chemical formula should be changed as follows:

Table 25
Compound B-134

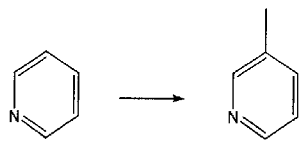

Signed and Sealed this

Twenty-seventh Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

<u>Column 14,</u>
Lines 46 and 48, delete "(1R)" and insert -- (1S) --;
Line 59, delete "C" and insert -- c -- (i.e. small letter).
Lines 64 and 66, delete "(1S)" and insert -- (1R) --.

<u>Column 15.</u>
Line 9, delete "C" and insert -- c -- (i.e. small letter).

<u>Column 17,</u>
Table 1, Example No. 7: the chemical formula should be changed as follows:

Table 1
Example 7

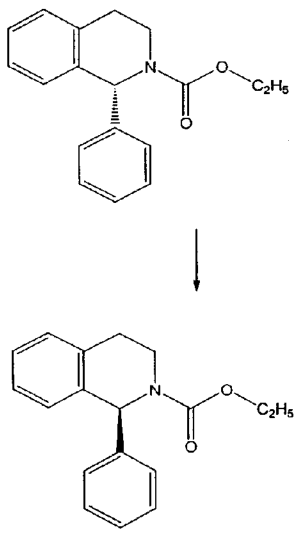

UNITED STATES PATENT AND TRADEMARK OFFICE

CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

<u>Column 17 cont'd,</u>
Table 1, Example No. 8: the chemical formula should be changed as follows:

Table 1
Example 8

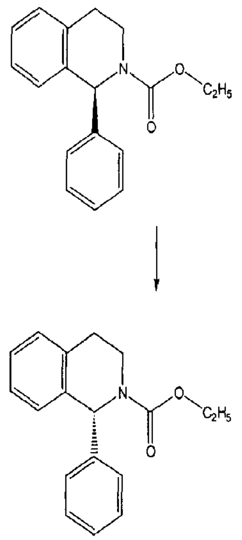

<u>Column 21,</u>
Lines 13 and 42, delete "(1R)" and insert -- (1S) --;
Line 28, delete "(1R,3'RS)" and insert -- (1S,3'RS) --; and
Line 62, delete "(1R,3'R)" and insert -- (1S,3'R) --.

<u>Column 22,</u>
Line 14, delete "(1S,3'S)" and insert -- (1R,3'S) --;
Lines 16 and 32, delete "(1S)" and insert -- (1R) --;
Line 30, delete "(1S,3'R)" and insert -- (1R,3'R) --;
Line 47, delete "(1R,3'S)" and insert -- (1S,3'S) --; and
Line 49, delete "(1R)" and insert -- (1S) --.

UNITED STATES PATENT AND TRADEMARK OFFICE

CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

Column 24,
Line 13, delete "(1R,3'R)" and insert -- (1S, 3'R) --;
Line 40, delete "(1R,3'R)" and insert -- (1S,3'R) --; and
Lines 25 and 45, delete "(1'R,3R)" and insert -- (1'S,3R) --.

Column 26,
Table 3, Example No. 7: the chemical formula should be changed as follows:

Table 3
Example 7

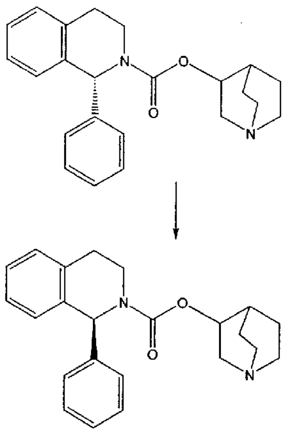

Table 3, Example No. 8: the chemical formula should be changed as follows:

Table 3
Example 8

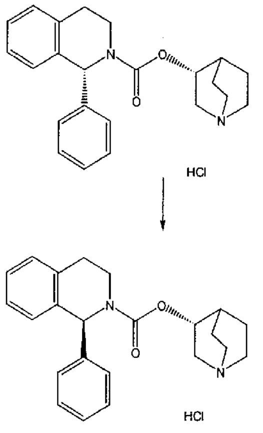

UNITED STATES PATENT AND TRADEMARK OFFICE

CERTIFICATE OF CORRECTION

PATENT NO. : 6,174,896 B1 
DATED : January 16, 2001
INVENTOR(S) : Mokoto Takeuchi et al.

It is certified that error appears in the above-identified patent and that said Letters Patent is hereby corrected as shown below:

<u>Column 26 cont'd,</u>
Table 3, Example No. 9: the chemical formula should be changed as follows:

Table 3
Example 9

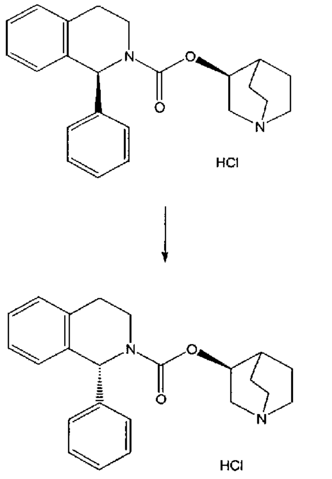

Table 3, Example No. 10: the chemical formula should be changed as follows:

Table 3
Example 10

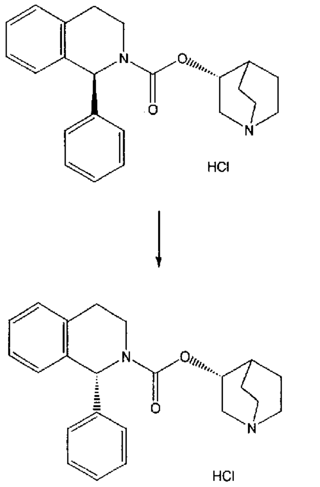

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 27,
Table 4, Example No. 11: the chemical formula should be changed as follows:

Table 4
Example 11

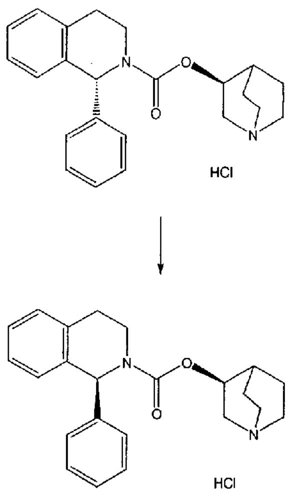

Column 28,
Table 4, Example No. 18: the chemical formula should be change as follows:

Table 4
Example 18

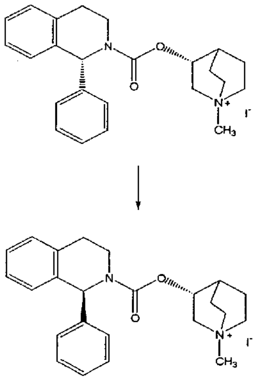

UNITED STATES PATENT AND TRADEMARK OFFICE
CERTIFICATE OF CORRECTION

PATENT NO. : 6,174,896 B1
DATED : January 16, 2001
INVENTOR(S) : Mokoto Takeuchi et al.

It is certified that error appears in the above-identified patent and that said Letters Patent is hereby corrected as shown below:

Column 61,
Table 25, Compound B-134: the chemical formula should be changed as follows:

Table 25
Compound B-134

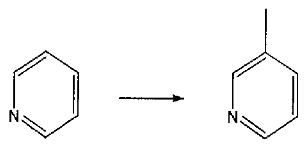

This certificate supersedes Certificate of Correction issued Twenty-seventh day of May, 2003.

Signed and Sealed this

Eighth Day of July, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,174,896 B1 
DATED : January 16, 2001
INVENTOR(S) : Makoto Takeuchi et al.

It is certified that error appears in the above-identified patent and that said Letters Patent is hereby corrected as shown below:

Column 14,
Lines 46 and 48, delete "(1R)" and insert -- (1S) --;
Line 59, delete "C" and insert -- c -- (i.e. small letter).
Lines 64 and 66, delete "(1S)" and insert -- (1R) --.

Column 15.
Line 9, delete "C" and insert -- c -- (i.e. small letter).

Column 17,
Table 1, Example No. 7: the chemical formula should be changed as follows:

Table 1
Example 7

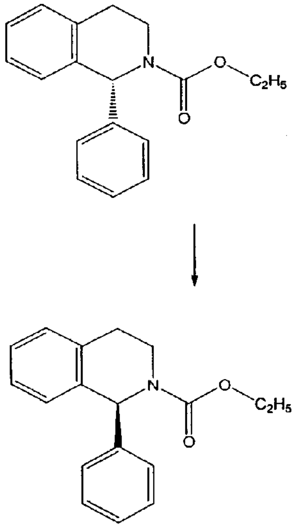

UNITED STATES PATENT AND TRADEMARK OFFICE
CERTIFICATE OF CORRECTION

PATENT NO. : 6,174,896 B1
DATED : January 16, 2001
INVENTOR(S) : Makoto Takeuchi et al.

It is certified that error appears in the above-identified patent and that said Letters Patent is hereby corrected as shown below:

Column 17 cont'd,
Table 1, Example No. 8: the chemical formula should be changed as follows:

Table 1
Example 8

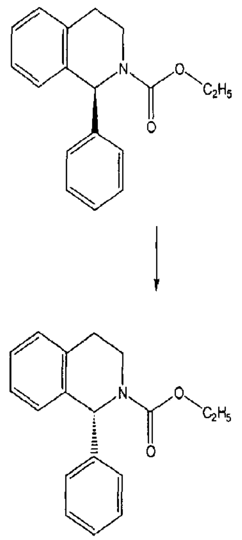

Column 21,
Lines 13 and 42, delete "(1R)" and insert -- (1S) --;
Line 28, delete "(1R,3'RS)" and insert -- (1S,3'RS) --; and
Line 62, delete "(1R,3'R)" and insert -- (1S,3'R) --.

Column 22,
Line 14, delete "(1S,3'S)" and insert -- (1R,3'S) --;
Lines 16 and 32, delete "(1S)" and insert -- (1R) --;
Line 30, delete "(1S,3'R)" and insert -- (1R,3'R) --;
Line 47, delete "(1R,3'S)" and insert -- (1S,3'S) --; and
Line 49, delete "(1R)" and insert -- (1S) --.

UNITED STATES PATENT AND TRADEMARK OFFICE

CERTIFICATE OF CORRECTION

PATENT NO. : 6,174,896 B1 
DATED : January 16, 2001
INVENTOR(S) : Makoto Takeuchi et al.

It is certified that error appears in the above-identified patent and that said Letters Patent is hereby corrected as shown below:

<u>Column 24,</u>
Line 13, delete "(1R,3'R)" and insert -- (1S, 3'R) --;
Line 40, delete "(1R,3'R)" and insert -- (1S,3'R) --; and
Lines 25 and 45, delete "(1'R,3R)" and insert -- (1'S,3R) --.

<u>Column 26,</u>
Table 3, Example No. 7: the chemical formula should be changed as follows:

Table 3
Example 7

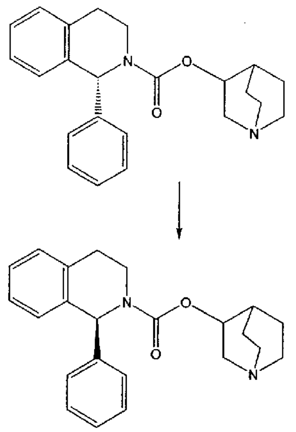

Table 3, Example No. 8: the chemical formula should be changed as follows:

Table 3
Example 8

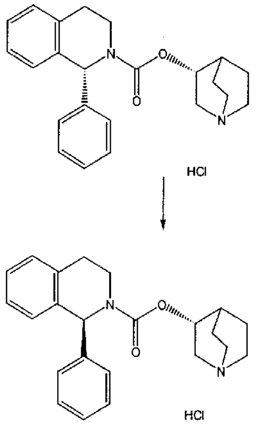

CERTIFICATE OF CORRECTION

PATENT NO. : 6,174,896 B1
DATED : January 16, 2001
INVENTOR(S) : Makoto Takeuchi et al.

It is certified that error appears in the above-identified patent and that said Letters Patent is hereby corrected as shown below:

Column 26 cont'd,

Table 3, Example No. 9: the chemical formula should be changed as follows:

Table 3
Example 9

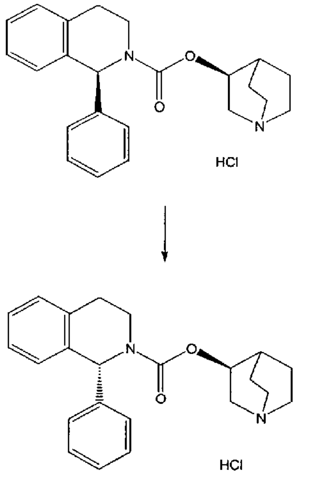

Table 3, Example No. 10: the chemical formula should be changed as follows:

Table 3
Example 10

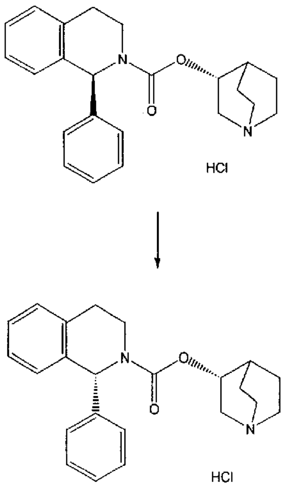

CERTIFICATE OF CORRECTION

PATENT NO. : 6,174,896 B1 
DATED : January 16, 2001
INVENTOR(S) : Makoto Takeuchi et al.

It is certified that error appears in the above-identified patent and that said Letters Patent is hereby corrected as shown below:

Column 27,
Table 4, Example No. 11: the chemical formula should be changed as follows:

Table 4
Example 11

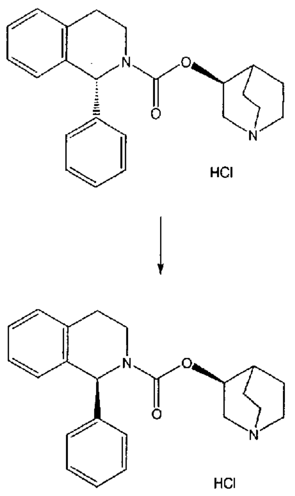

Column 28,
Table 4, Example No. 18: the chemical formula should be change as follows:

Table 4
Example 18

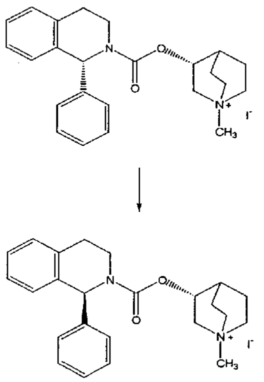

UNITED STATES PATENT AND TRADEMARK OFFICE
CERTIFICATE OF CORRECTION

PATENT NO. : 6,174,896 B1
DATED : January 16, 2001
INVENTOR(S) : Makoto Takeuchi et al.

It is certified that error appears in the above-identified patent and that said Letters Patent is hereby corrected as shown below:

Column 61,
Table 25, Compound B-134: the chemical formula should be changed as follows:

Table 25
Compound B-134

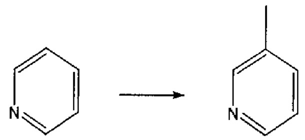

This certificate supersedes Certificate of Correction issued July 8, 2003.

Signed and Sealed this

Fifth Day of August, 2003

JAMES E. ROGAN
*Director of the United States Patent and Trademark Office*